(12) United States Patent
Hodges et al.

(10) Patent No.: US 12,258,638 B2
(45) Date of Patent: Mar. 25, 2025

(54) AIRBORNE PATHOGEN SIMULANTS AND MOBILITY TESTING

(71) Applicant: SafeTraces, Inc., Pleasanton, CA (US)

(72) Inventors: Ulrike W. Hodges, Berkeley, CA (US); Quin Chou, Pleasanton, CA (US); Erik Malmstrom, San Jose, CA (US); Phil M. Arnold, Redwood City, CA (US)

(73) Assignee: SafeTraces, Inc., Pleasanton, CA (US)

( * ) Notice: Subject to any disclaimer, the term of this patent is extended or adjusted under 35 U.S.C. 154(b) by 96 days.

(21) Appl. No.: 17/165,935

(22) Filed: Feb. 2, 2021

(65) Prior Publication Data

US 2021/0324485 A1   Oct. 21, 2021

Related U.S. Application Data

(60) Provisional application No. 63/066,076, filed on Aug. 14, 2020, provisional application No. 63/011,176, filed on Apr. 16, 2020.

(51) Int. Cl.
| | | |
|---|---|---|
| C12Q 1/70 | (2006.01) | |
| C12Q 1/68 | (2018.01) | |
| C12Q 1/6825 | (2018.01) | |
| C12Q 1/6851 | (2018.01) | |
| C12Q 1/686 | (2018.01) | |

(52) U.S. Cl.
CPC ............... *C12Q 1/701* (2013.01); *C12Q 1/68* (2013.01); *C12Q 1/6825* (2013.01); *C12Q 1/6851* (2013.01); *C12Q 1/686* (2013.01)

(58) Field of Classification Search
CPC ........ C12Q 1/701; C12Q 1/68; C12Q 1/6825; C12Q 1/6851; C12Q 1/686; C12N 15/1017
See application file for complete search history.

(56) References Cited

U.S. PATENT DOCUMENTS

| | | |
|---|---|---|
| 1,913,069 A | 6/1933 | Chance |
| 4,593,360 A | 6/1986 | Cocks |
| 6,312,911 B1 | 11/2001 | Bancroft et al. |
| 6,532,835 B1 * | 3/2003 | Saaski .................. G01N 1/2273 73/863.21 |
| 8,293,535 B2 | 10/2012 | Farquar et al. |
| 10,556,032 B2 | 2/2020 | Zografos et al. |
| 11,087,888 B2 | 8/2021 | Chatterjea et al. |
| 11,129,915 B2 | 9/2021 | Zografos et al. |
| 2002/0129523 A1 | 9/2002 | Hunt |

(Continued)

FOREIGN PATENT DOCUMENTS

| | | |
|---|---|---|
| CN | 101379188 A | 3/2009 |
| CN | 104024426 A | 9/2014 |

(Continued)

OTHER PUBLICATIONS

Wan et al., Aerosol Science and Technology, 43: 322-343, (Year: 2009).*

(Continued)

*Primary Examiner* — Seung H Lee
(74) *Attorney, Agent, or Firm* — Haynes and Boone, LLP

(57) ABSTRACT

Airborne pathogen mobility and the airborne mobility of respiratory droplets, such as saliva, and testing thereof, can be monitored by tracking detectable compounds and measuring concentrations.

23 Claims, 14 Drawing Sheets

(56) References Cited

U.S. PATENT DOCUMENTS

| | | | |
|---|---|---|---|
| 2004/0166520 A1 | 8/2004 | Connolly | |
| 2005/0031487 A1 | 2/2005 | Rosenblatt et al. | |
| 2005/0042604 A1* | 2/2005 | Tong | C12Q 1/04 435/5 |
| 2006/0037222 A1 | 2/2006 | Hunt et al. | |
| 2006/0111845 A1 | 5/2006 | Forbis et al. | |
| 2009/0070134 A1 | 3/2009 | Rodgers | |
| 2010/0159434 A1 | 6/2010 | Lampotang et al. | |
| 2010/0261193 A1 | 10/2010 | Webster et al. | |
| 2011/0165569 A1 | 7/2011 | Macula | |
| 2011/0177539 A1 | 7/2011 | Sutton et al. | |
| 2012/0112883 A1 | 5/2012 | Wallace et al. | |
| 2013/0052751 A1 | 2/2013 | Farquar et al. | |
| 2013/0122807 A1 | 5/2013 | Tenarvitz et al. | |
| 2014/0046722 A1 | 2/2014 | Rosenbloom et al. | |
| 2014/0057276 A1 | 2/2014 | Farquar et al. | |
| 2014/0108039 A1 | 4/2014 | Rensvold et al. | |
| 2014/0167917 A2 | 6/2014 | Wallace et al. | |
| 2014/0220576 A1 | 8/2014 | Macula | |
| 2014/0255984 A1 | 9/2014 | Sharpin | |
| 2014/0272097 A1 | 9/2014 | Jung et al. | |
| 2014/0340423 A1 | 11/2014 | Taylor et al. | |
| 2015/0034309 A1 | 2/2015 | Blair | |
| 2015/0205985 A1 | 7/2015 | Jinadatha | |
| 2015/0314026 A1 | 11/2015 | Mauzerall et al. | |
| 2015/0322426 A1 | 11/2015 | Zografos et al. | |
| 2015/0361490 A1 | 12/2015 | Farquar et al. | |
| 2016/0038083 A1 | 2/2016 | Ding et al. | |
| 2016/0102335 A1 | 4/2016 | Franciskovich et al. | |
| 2016/0171179 A1 | 6/2016 | Donofrio et al. | |
| 2016/0188943 A1 | 6/2016 | Franz | |
| 2016/0306934 A1 | 10/2016 | Sperry et al. | |
| 2016/0307459 A1 | 10/2016 | Chestnut et al. | |
| 2017/0038353 A1 | 2/2017 | Zografos et al. | |
| 2017/0081707 A1 | 3/2017 | Dillon et al. | |
| 2017/0197002 A1 | 7/2017 | Dobrinsky et al. | |
| 2017/0322701 A1 | 11/2017 | Bowman et al. | |
| 2017/0333859 A1 | 11/2017 | Lind | |
| 2018/0108178 A1 | 4/2018 | Murugappan et al. | |
| 2018/0126021 A1 | 5/2018 | Valentine et al. | |
| 2018/0252738 A1 | 9/2018 | Denney | |
| 2018/0369438 A1 | 12/2018 | Grossman et al. | |
| 2019/0029002 A1 | 1/2019 | Kotzer et al. | |
| 2019/0086296 A1 | 3/2019 | West | |
| 2019/0087533 A1 | 3/2019 | O'Hara | |
| 2019/0120727 A1 | 4/2019 | Harding et al. | |
| 2019/0211324 A1 | 7/2019 | Zografos et al. | |
| 2019/0241982 A1 | 8/2019 | Hogan et al. | |
| 2019/0318807 A1 | 10/2019 | O'Hara et al. | |

FOREIGN PATENT DOCUMENTS

| | | |
|---|---|---|
| CN | 104131008 A | 11/2014 |
| CN | 104513863 A | 4/2015 |
| WO | 2004063856 A2 | 7/2004 |
| WO | 2008083323 A9 | 9/2008 |
| WO | 2008137831 A1 | 11/2008 |
| WO | 2011163296 A2 | 12/2011 |
| WO | 2012037876 A1 | 3/2012 |
| WO | 2014164958 A1 | 10/2014 |
| WO | 2017049160 A2 | 3/2017 |
| WO | 2017096110 A1 | 6/2017 |
| WO | 2019157227 A1 | 8/2019 |

OTHER PUBLICATIONS

Pan et al., "Collection, Particle Sizing and Detection of Airborne Viruses," Journal of Applied Microbiology 127:1596-1611 (2019) [doi=10.1111/jam.14278].

International Search Report issued in PCT Application No. PCT/US2021/027495, mailed on Dec. 8, 2021.

Andrews, "DNA Spray-On Technology Could Revolutionize Food Traceability", Food Safety News, http://www.foodsafetynews.com/2014/11/dna-laced-spray-technology-could-revolutionize-food-traceability/#.W1kRNNVKjRY, 2014, 2 pages.

Busta et al., "The Use of Indicators and Surrogate Microorganisms for the Evaluation of Pathogens in Fresh and Fresh-Cut Produce", Comprehensive Reviews in Food Science and Food Safety, vol. 2 (Supplement), 2003, pp. 179-185.

Bystrykh, "Generalized DNA Barcode Design Based on Hamming Codes", PLOS One, vol. 7(5):e36852, 2012, 8 pages.

Danyluk, "Process Validation: Selection and Use of Surrogates", University of Florida, Institute of Food and Agricultural Sciences, presentation dated Apr. 2014, 19 pages.

European Supplementary Search Report dated Jun. 15, 2018 in European Patent Application No. 15878244.1, 1 page.

European Supplementary Search Report dated Feb. 7, 2019 in European Patent Application No. 16833458.9, 1 page.

European Supplementary Search Report dated Oct. 1, 2020 in European Patent Application No. 19738614.7, 1 page.

Farquar, "DNATrax (DNA Tagged Reagents for Aerosol experiments)", Lawrence Livermore National Laboratory, presentation LLNL-PRES-642415, 2013, retrieved from the Internet at https://ipo.llnl.gov/success/multimedia/dnatrax-dna-tagged-reagents-aerosol-experiments-george-farquar-llnl-scientist, 8 pages.

Galimberti et al., "DNA Barcoding as a New Tool for Food Traceability", Food Research International, vol. 50(I), 2013, pp. 55-63.

Galimberti et al., "DNA Barcoding for Minor Crops and Food Traceability", Hindawi Publishing Corporation, Advances in Agriculture, vol. 2014, Article ID 831875, 2014, pp. 1-8.

Harding et al., "Unique DNA-barcoded Aerosol Test Particles for Studying Aerosol Transport", Aerosol Science and Technology, vol. 50(5), 2016, pp. 429-435.

Hou et al., "Rapid Bioparticle Concentration and Detection by Combining a Discharge Driven Vortex with Surface Enhanced Raman Scattering", Biomicrofluidics 1, 014106, 2007, pp. 1-13.

International Search Report mailed Aug. 12, 2015 in International Patent Application No. PCT/US2015/028880, 3 pages.

International Search Report mailed Sep. 8, 2016 in International Patent Application No. PCT/US2016/038083, 2 pages.

International Search Report mailed Mar. 15, 2019 in International Patent Application No. PCT/US2019/013069, 2 pages.

International Search Report mailed Aug. 9, 2019 in International Patent Application No. PCT/ US2019/029002, 2 pages.

Ma et al., "Development of Thermal Surrogate Microorganisms in Ground Beef for In-Plant Critical Control Point Validation Studies", Journal of Food Protection, vol. 70(4), 2007, pp. 952-957.

Naaum, "Novel Methods of Species and Product Authenticity and Traceability Testing Using DNA Analysis for Food and Agricultural Applications", Doctoral Dissertation, Department of Integrative Biology, University of Guelph, 2014, 144 pages.

Niebuhr et al., "Evaluation of Nonpathogenic Surrogate Bacteria as Process Validation Indicators for *Salmonella enterica* for Selected Antimicrobial Treatments, Cold Storage and Fermentation in Meat", Journal of Food Protection, 71(4), 2008, pp. 714-718.

Oxford Gene Technology, "DNA Storage and Quality," Aug. 22, 2011, retrieved from the Internet at http://www.ogt.com/resources/literature/403_dna_storage_and_quality, 5 pages.

Puddu et al., "Magnetically Recoverable, Thermostable, Hydrophobic DNA/Silica Encapsulates and Their Application as Invisible Oil Tags" ACS Nano, vol. 8(3), 2014, pp. 2677-2685.

Ruther, "Assistive Systems for Quality Assurance by Context-aware User Interfaces in Health Care and Production", Dissertation, Faculty of Technology, Bielefeld University, 2014, 168 pages.

Sharma et al., "Hydrological Tracers Using Nanobiotechnology: Proof of Concept", Environmental Science and Technology, vol. 46(16), 2012, pp. 8928-8936.

Sinclair et al., "A Criteria for Selection of Surrogates Used to Study the Fate and Control of Pathogens in the Environment", Applied and Environmental Microbiology, vol. 78(6), 2012, pp. 1969-1977.

Yeater et al., "Effectiveness of Sanitizing Products on Controlling Selected Pathogen Surrogates on Retail Deli Slicers", Journal of Food Protection, vol. 78(4), 2015, pp. 707-715.

Extended European Search Report mailed Apr. 3, 2024, European Patent Application No. 21811937.8, filed Apr. 15, 2021, 7 pages.

(56) References Cited

OTHER PUBLICATIONS

Singh et al., "Coronavirus-mimicking nanoparticles (CorNPs) in artificial saliva droplets and nanoaerosols: Influence of shape and environmental factors on particokinetics/particle aerodynamics", Science of Total Environment, Elsevier, Amsterdam, NL, vol. 860, Nov. 25, 2022, XP087245546, ISSN: 0048-9697, https://doi.org/10.1016/j.scitotenv.2022.160503.

International Search Report issued in PCT Application No. PCT/US2021/016065, mailed on May 24, 2021.

Kumar et al., "A rapid screening for adulterants in olive oil using DNA barcodes." Food Chemistry 127.3 (2011):1335-1341 (Year: 2011), pp. 1336-1341.

Leier et al., "Cryptography with DNA binary strands." Biosystems 57 .1 (2000): 13-22. (Year: 2000), pp. 13-22.

Ovissipour et al., "DNA-based surrogate indicator for sanitation verification and predict inactivation of *Escherichia coli* O157:H7 using vibrational spectroscopy (FTIR)." Food Control 100 (2019): 67-77 (Year: 2019), pp. 67-77.

Singh et al., "DNA QR coding for data security using DNA sequence." International Journal of Information Technology 12.2 (Jan. 18, 2020): 571-576 (Year: 2020), pp. 571-576.

Vassou et al., "DNA barcoding for species identification from dried and powdered plant parts: A case study with authentication of the raw drug market samples of Sida cordifolia." Gene 559.1 (2015): 86-93 (Year:2015), pp. 86-93.

Yaari et al., "Theranostic barcoded nanoparticles for personalized cancer medicine." Nature communications 7.1 (2016): 13325 (Year: 2016), pp. 1-10.

\* cited by examiner

| | Spray |
|---|---|
| 1 | Qualified professionals release airborne tracers having simulants at release locations, with the tracers including DNA taggants |
| 2 | Circulate<br>Airborne tracers disperse through building/indoor structure spaces, air ducting, etc. |
| 3 | Sample<br>Air samples are collected at selected collection locations at selected collection times and tested or preserved for later testing |
| 4 | Results<br>The diagnostic report provides results, perhaps as a heat map visualization, dilution and filtration plots, etc. to guide engineering and HVAC control decisions |

FIG. 3

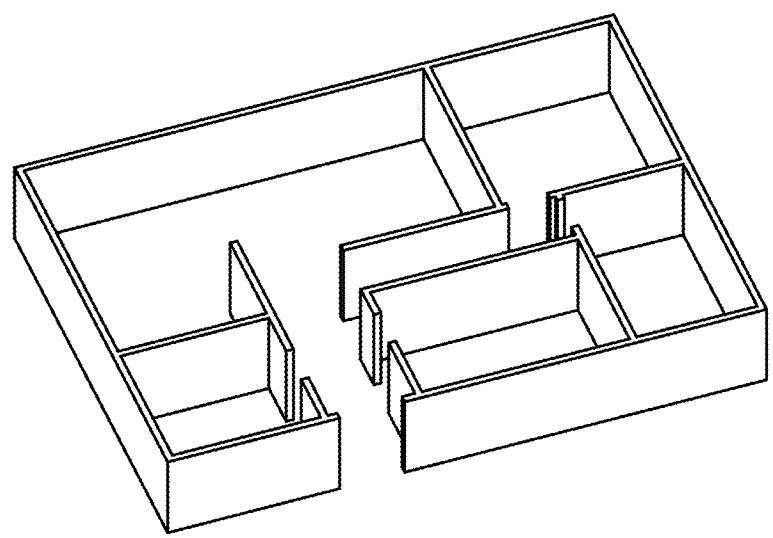
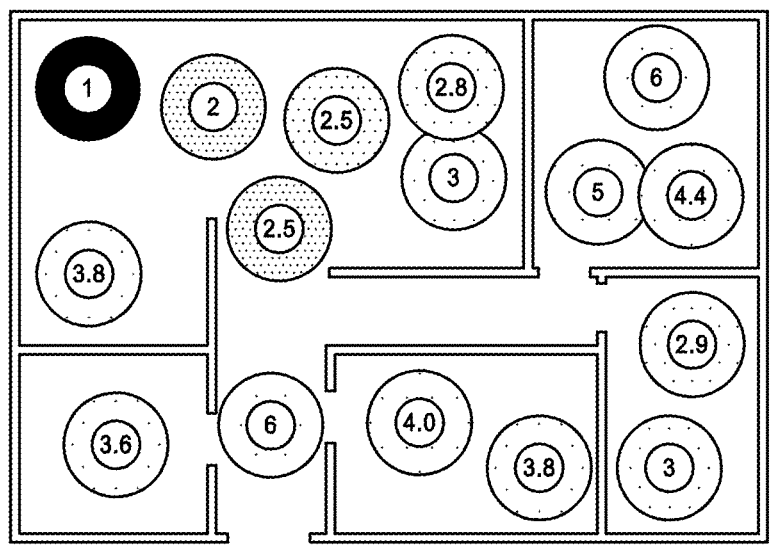
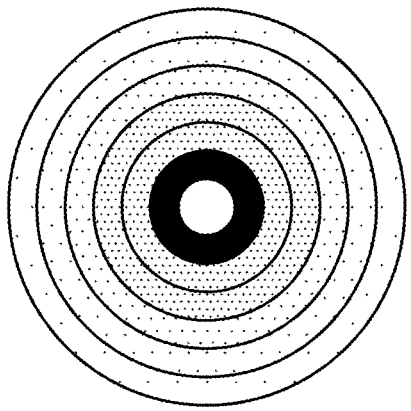
FIG. 7

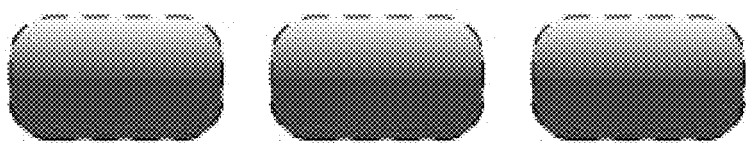
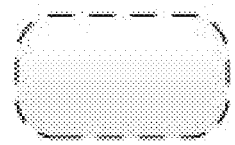
FIG. 13

AIRBORNE PATHOGEN SIMULANTS AND MOBILITY TESTING

CROSS-REFERENCES TO PRIORITY AND RELATED APPLICATIONS

This application claims the benefit of, and priority from, U.S. Provisional Patent Application No. 63/011,176 filed Apr. 16, 2020, entitled "Airborne Pathogen Mobility Testing" and U.S. Provisional Patent Application No. 63/066,076 filed Aug. 14, 2020, entitled "Airborne Pathogen Mobility Testing."

Other applications/patents:
  (1) U.S. Pat. No. 10,302,614 issued May 28, 2019 to Zografos, et al. entitled "DNA Based Bar Code for Improved Food Traceability" (hereinafter "Zografos I");
  (2) U.S. Pat. No. 10,556,032 issued Feb. 11, 2020 to Zografos, et al. entitled "Sanitation Monitoring System Using Pathogen Simulants and Simulant Tracking (hereinafter "Zografos II");
  (3) U.S. Pre-Grant Publication 2017/0038353 published Feb. 9, 2017 naming Zografos, et al. and entitled "Pathogen Simulants Based on Encapsulated Tagged DNA for Verification of Sanitation and Wash Water Systems for Fresh Produce" (hereinafter "Zografos III").

The entire disclosures of the applications recited above are hereby incorporated by reference, as if set forth in full in this document, for all purposes.

FIELD

The present disclosure generally relates to use of pathogen simulants for evaluating conditions in an environment where pathogens could exist and relates more particularly to methods and apparatus for tracking the airborne mobility of respiratory droplets, such as saliva, and potential airborne pathogen flows using pathogen simulants.

BACKGROUND

Pathogens, such as viruses, can be transmitted through the air. This is particularly a problem in buildings and particular pathogens, such as SARS-CoV-2, have been shown to have infection rates vary based on indoor airflow patterns. SARS-CoV-2 creates a significant public health and safety risk in the built environment, with some experts emphasizing the importance of airborne transmission via respiratory droplets that aerosolize, stay suspended in air for hours, and travel significantly beyond a droplet transmission zone around a person who is shedding the SARS-CoV-2 virus. Aerosols have been shown to contain SARS-CoV-2 virus. As a result, the virus can travel further from a person shedding the virus than a typical droplet transmission zone, which is usually approximated as six feet or two meters. It is known that smaller exhaled droplets can behave as an aerosol, rather than as a ballistic droplet.

Some research has indicated that aerosol inhalation could be a dominant contributor to SARS-CoV-2 transmission in close quarters, such as passengers aboard a cruise ship, which can result in widespread COVID-19 illnesses. Changes in heating, ventilating, and air conditioning (HVAC) systems might be needed to limit such exposures but designs of HVAC systems might have to be done without information about what those exposures might be or based on crude approximations of airflow or based on idealized testing. Many facilities and engineering organizations might have to operate with insufficient data in the face of a once-in-a-century pandemic, with life-and-death safety consequences and enormous financial cost, risk, and liability at stake, as it might relate to assessing the risk of airborne pathogen transmission indoors.

There is a need to understand the airborne mobility and virulence of a various pathogens and their carriers (such as water, saliva, humid air, dust, etc.) in order to monitor conditions and take corrective actions if necessary. This understanding extends to a need to understand multiple airflows and in environments with multiple airflows, there might be a need to test multiple paths in parallel, possibly involving intersecting or intermixing paths over which air might flow and carry potential pathogens. Where the spaces are occupied and/or where it is impractical or inadvisable to use the pathogens themselves, alternatives are needed.

SUMMARY

Embodiments of the invention include technologies related to airborne pathogen mobility and the airborne mobility of respiratory droplets, such as saliva, and testing thereof, as described herein. The following detailed description together with the accompanying drawings will provide a better understanding of the nature and advantages of the present invention.

A composition comprising a saliva simulant might be provided, wherein the saliva simulant comprises a DNA taggant, water, and a carrier, the saliva simulant having been determined or characterized to have a behavior suitable for simulating human emission of a target pathogen. The specific target pathogen might be SARS-Cov-2. The carrier might comprise polysaccharides, proteins, salt, or a combination thereof.

A method of providing a saliva simulant is providing comprising combining a DNA taggant with water and a carrier to form the saliva simulant, and determining that
  the saliva simulant has a behavior suitable for simulating human emission of a target pathogen.

A method of distributing a saliva simulant is provided, comprising receiving the saliva simulant, wherein the saliva simulant comprises water, a DNA taggant, and a carrier, and wherein the saliva simulant is configured to have a behavior suitable for simulating human emission of a target pathogen, and spraying the saliva simulant at a first release location, to be detected at a first collection location.

The first release location and the first collection location might be separated by building infrastructure. The first release location and the first collection location might be such that measurable airflow occurs from the first release location to the first collection location. The first release location and the first collection location might both be within a confined space in a building, with the saliva simulant released at the first release location at a first time and a portion of released saliva simulant collected at the first collection location at a second time, wherein the second time is after, and distinct from, the first time.

A method of detecting a pathogen simulant can be provided, comprising determining a plurality of locations to receive a saliva simulant released in air, wherein the saliva simulant comprises water, a DNA taggant, and a carrier, the saliva simulant having been determined or characterized to have a behavior suitable for simulating human emission of a target pathogen, collecting a sample at each location of the plurality of locations, and determining an amount of the saliva simulant in the sample.

A sprayer for spraying a saliva simulant might be provided, comprising a container containing the saliva simulant, wherein the saliva simulant comprises water, a DNA taggant, and a carrier, a trigger connected to the container and configured to spray the saliva simulant out into an airspace at a rate that corresponds to saliva dispersion of a human into the airspace resulting from the human coughing, sneezing, talking, yelling, and/or singing. For example, the sprayer might be computer-controlled and emit ten or twelve, or some other number of sprays, to emulate talking and a larger number of sprays to emulate singing, and an even larger number of sprays to emulate coughing or sneezing. For some sprayers, simulant volume is controllable as well as emission velocity.

An air sampler for collecting an air sample might be provided, comprising a vacuum apparatus configured to collect the air sample from an ambient environment and to have a vacuum flow rate that matches human breathing, and a filter connected to the vacuum apparatus and configured to have a pore size suitable for filtering a saliva simulant from the air sample.

A system might comprise a sprayer configured to release a saliva simulant, and an air sampler configured to collect an air sample at a plurality of locations determined to receive a portion of released saliva simulant released in air.

A method for displaying movement of a saliva simulant might be provided, comprising receiving information of a first amount of the saliva simulant at a first location where the saliva simulant is released in air and of a second amount of the saliva simulant detected a second location that is different from the first location, wherein the saliva simulant comprises water, a DNA taggant, and a carrier, the saliva simulant having a characteristic, such as evaporation rate or other characteristic, that matches or simulates saliva, and generating a report displaying a first graphic element representing the first amount of the saliva simulant at the first location and displaying a second graphic element representing the second amount of the saliva simulant at the second location in a map comprising the first location and the second location.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the surface computation method, as defined in the claims, is provided in the following written description of various embodiments of the disclosure and illustrated in the accompanying drawings.

BRIEF DESCRIPTION OF THE DRAWINGS

Those of skill in the art will understand that the drawings, described below, are for illustrative purposes only. The drawings are not intended to limit the scope of the present teachings in any way.

FIG. 2 illustrates an example test setup according to an embodiment.

FIG. 3 depicts a process for testing and evaluating a space for possible airborne pathogen travel according to an embodiment.

FIG. 7 illustrates a building layout and a corresponding bullseye visualization according to an embodiment.

FIG. 13 illustrates an example of a saliva simulant that contains a DNA taggant bound to a carrier polysaccharide, depicting an electrophoretic mobility shift assay to detect binding of a DNA taggant to a carrier polysaccharide.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described. Unless otherwise noted, terms are to be understood according to conventional usage by those of ordinary skill in the relevant art.

There is a significant risk of transmission of airborne pathogens in buildings, particularly in buildings such as non-medical buildings where pathogen travel might not have been a design consideration when constructed. More generally, these are concerns for enclosed spaces, partially enclosed spaces, and the like, whether fixed or mobile (e.g., airplanes, aircraft carriers, submarines, etc.) but most examples in this description use a building as an example.

Some viruses, such as, for example, the severe acute respiratory syndrome coronavirus 2 (SARS-CoV-2) that causes coronavirus disease 2019 (COVID-19) are transmissible through respiratory droplets. In the case of SARS-CoV-2, which is a highly contagious pathogenic virus, these respiratory droplets have been reported to live on surfaces for days and float in the air for three hours or more. Many buildings are not necessarily designed to limit airflow based on airborne pathogen or pollutant travel, as a laboratory-level clean room might. Offices, hotels, and other non-medical buildings or structures (e.g., aircraft, ships, etc.) might have poor air ventilation, significantly increasing the risk of spreading a particular virus, such as SARS-CoV-2, through a building and infecting those individuals therein.

Figure 1:
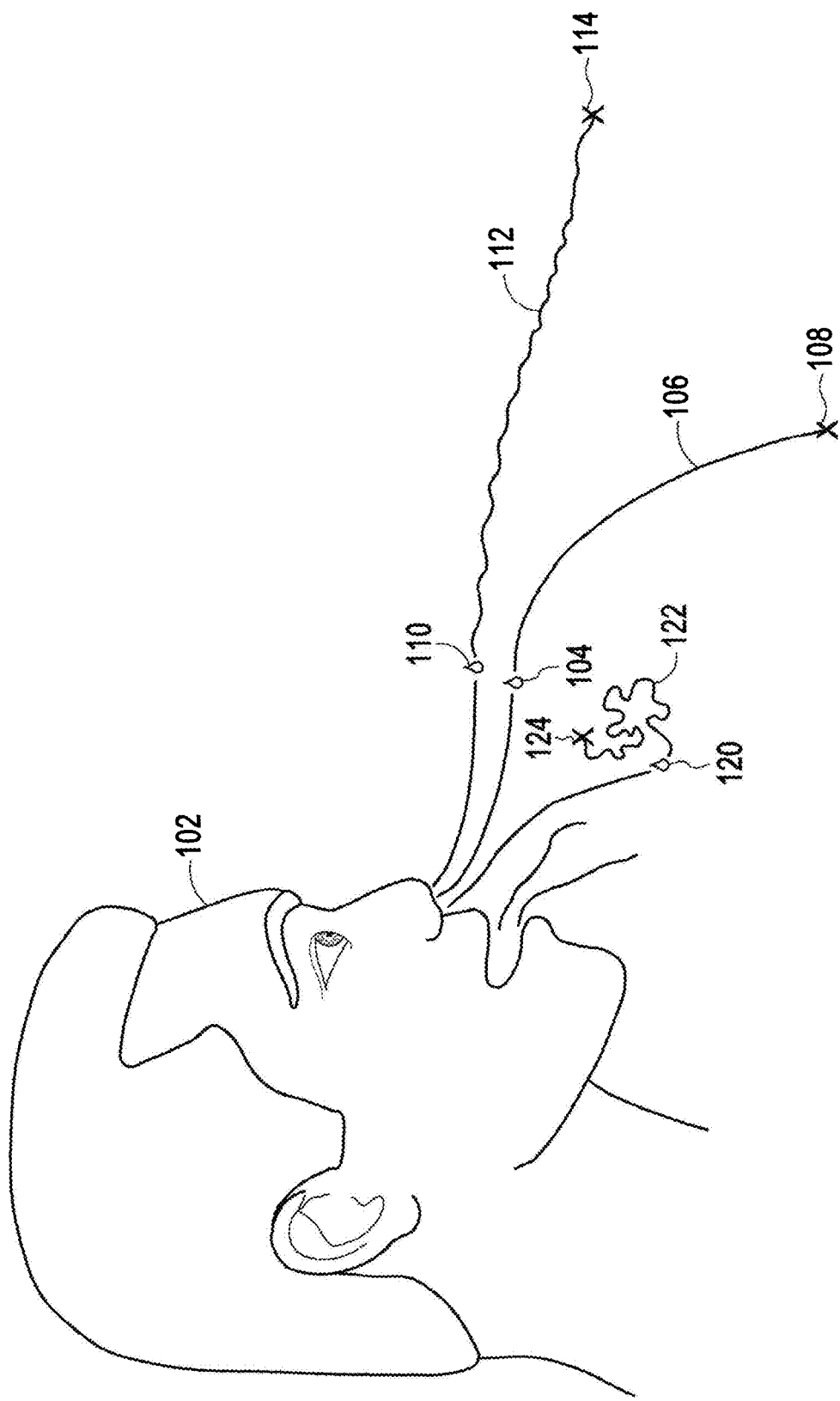
FIG. 1 illustrates examples of airflows from a person to an environment.

FIG. 1 illustrates examples of airflows from a person to an environment. The environment might include other people. Where surface contamination is a concern, determining what surfaces other people might touch can be tracked. Where airborne transmission is a primary concern, the airflow from a person and their expelled saliva might be modelled. When speaking, singing, talking, or just breathing, a person 102 exhales air from their mouth and/or nose. Some of what is exhaled is oxygen, nitrogen, carbon dioxide and gaseous water vapor, which as gasses, readily mix with nearby environmental air. However, some of what is exhaled is in liquid and/or solid form. Some of that might be larger particles, such as particle 104, that would follow a largely parabolic path 106 and land at a ground disposition location 108. The distance from person 102 to ground disposition location 108 is typically a function of the height difference between the height at exhalation and the height of ground disposition location 108 and the velocity of the particle at exhalation. While sneezing might provide for a higher exhalation velocity, the travel distance of a large droplet resulting from a sneeze is limited and is easily modeled. On the other hand, a droplet 110 that is exhaled and is small enough that it behaves as an aerosol particle suspended in the air can travel along a path 112 to a location 114 to possibly be inhaled by another person, where the distance from person 102 to location 114 is primarily a function of how environmental air is circulating. Another concern is particles, such as particle 120, that follow paths that allow the particles to remain aloft, such as path 112, to a location 124 that is nearby, which is more of a particle being exhaled at one time and being present in the same space a considerable time later rather than the particle being exhaled at one place and being present at some later time at some distance away.

As illustrated, different ranges of particle sizes have different behaviors, so a saliva simulant with a particle size could be selected to model saliva movement well. A suitable simulant might model the expected or estimated distribution of droplet particle size, droplet nuclei particle size, evaporation rates (possibly taking into account humidity, temperature, and other factors), etc.

A method for displaying movement of a saliva simulant might be provided, comprising receiving information of a first amount of the saliva simulant at a first location where the saliva simulant is released in air and of a second amount of the saliva simulant detected a second location that is different from the first location, wherein the saliva simulant comprises water, a DNA taggant, and a carrier, the saliva simulant having a characteristic, such as evaporation rate or other characteristic, that matches or simulates saliva, and generating a report displaying a first graphic element representing the first amount of the saliva simulant at the first location and displaying a second graphic element representing the second amount of the saliva simulant at the second location in a map comprising the first location and the second location.

Saliva simulant droplet size might be controlled by composition and/or by the spraying mechanism used. For example, droplets size might be such that they fall after emission as would some saliva or as aerosols that can be kept aloft due to air movement. The saliva simulant can be constructed to have an evaporation rate similar to that of saliva.

Some pathogens, such as SARS-CoV-2, might be present in excretions and could become airborne by processes other than exhalation, such as by strong toilet flushing after elimination by an infected individual, which would cause pathogens to move around an indoor space and/or remain in an enclosed space for some time.

A building's HVAC systems might not bring in much, if any, fresh air. They instead might recirculate the air that is already inside, which generally includes a mix of carbon dioxide from exhalations, chemicals that off-gassed from building and decorating materials, and airborne pathogens, such as SARS-CoV-2. Improving air filtration therefore can be an effective way of limiting the spread of airborne pathogens, such as SARS-CoV-2, within buildings. Unfortunately, there are often other considerations that prevent adequate air filtration, including knowing where and when to filter.

Many existing solutions for verifying airflow are not capable of adequately approximate mobility of airborne pathogens, such as SARS-CoV-2. Other solutions, such as using tracer gas (e.g., sulfur hexafluoride), smoke, bubbles, balloons, or pressure testing, are lacking in various ways. For example, some systems cannot test filters, have limited equipment availability, cannot identify large versus localized problems, and/or are challenging to use.

The methods, apparatus, and technology described herein might be used to simulate airborne mobility of airborne pathogens, such as SARS-CoV-2, in order to support rapid environmental assessments, drive corrective actions (such as, for example, extra air filtration solutions in the short term and building design change in the long term), and mitigate risk of pathogen spread.

When there is concern with respect to a particular airborne pathogen, property and hotel management companies might be compelled to de-risk offices, hotels, and other shared buildings by occupants and public health authorities. The presently described airborne pathogen simulants can provide a standard way of certifying buildings initially and testing on routine basis afterwards, possibly including testing multiple airflow pathways in parallel even when those airflow pathways intersect and/or intermix.

In some embodiments, a first simulated concentration or first viral load is determined at a source location where a tagged pathogen simulant is released into the air and a second simulated concentration or second viral load is measured and/or determined at a target location and a ratio between those concentrations or loads can be used as an indicator of how problematic or non-problematic the airflow from the source location to the target location is. For example, the first simulated concentration might be higher or lower than an actual concentration of a pathogen at the course location, perhaps to make detection easier or more robust, but by considering the ratio, a facilities manager might be able to determine how much of a viral load that might be shed in one place in a building might appear at another location in the building. With this, the facilities manager might be able to determine that although there is some aerosol carrying from one place to another, the ratio and the amount of viral load likely to be present at the source would or would not be problematic at the target location based on an understanding that some threshold viral load might be needed to create adverse health effects.

In a specific example, the facilities manager might have an automated system that releases food-safe, aerosolized or aerosolizable pathogen simulants at a somewhat high concentration in a hotel lobby (perhaps at a particles/liter amount much higher than what would be expected from viral shedding of symptomatic or asymptomatic guests entering and/or remaining in the hotel lobby) and an automated system that samples air in a banquet hall to determine a concentration of the pathogen simulants in the banquet hall, either over time or as snapshots in time. A computer system controlling the automated processes might then compute a ratio of the source concentration to the target concentration, multiplied by an expected viral load concentration of the actual pathogen, to determine an estimated viral load that might appear in the banquet hall as a result of air transport.

The source and target can be the same location, separated in time, such as releasing the tracing aerosol in a more or less enclosed space, such as a restroom or conference room, to determine a ratio between pathogen simulant concentration at a release time in that space to pathogen simulant concentration in that same space at a later sampling time. This might be useful to determine how long it might take for a room to recover from a shedding event or a suspected shedding event.

The reduction ratio might be expressed logarithmically. Multiple tests can be run overlapping in time and/or space, using distinct DNA tags for pathogen simulants in tests for airflow that might overlap in time and/or space.

Example Embodiments

In one embodiment, a diagnostic system for safely assessing airborne pathogen risk in a built environment that enables facility managers to identify hotspots, assess ventilation and filtration, and inform remediations, might use a traceable saliva simulant that mimics transport, evaporation, etc. characteristics of exhaled saliva. Traceability might be accomplished by using a DNA taggant and a carrier, whereby small quantities of the DNA taggant can be detecting using, for example, PCR techniques. The sampling and testing processes might be able to detect and quantify over a wide range of results, such as five or six or more orders of magnitude.

The saliva simulant might have a chemical composition that mimics a chemical composition of human saliva and aerosols. In a specific embodiment, the saliva simulant comprises distilled water, food-grade, water-soluble ingredients, and a DNA taggant, wherein the DNA taggant might comprise a noncoding short segment of DNA.

In some embodiments, the DNA taggant used comprises copies of the same noncoding short segment of DNA. In other embodiments, an airborne tracer might have more than one DNA taggant and different DNA taggants might be used to encode information about the saliva simulant application. For example, a set of N distinct DNA taggants might be deployed and the presence or absence of particular DNA taggants could be the encoding of the information. In a specific example, where N=5 and there are five distinct DNA taggants deployed, if (a, b, c, d, e) denotes a taggant pattern, a first saliva simulant with the DNA taggant pattern (1, 1, 0, 0, 1) might be released at a first release location while a second saliva simulant with the DNA taggant pattern (0, 0, 1, 1, 1) might be released at a second release location. Samples can be collected at one or more collection locations and because the DN taggant patterns are distinct, the aerosol airflow from the first release location to a collection location can be distinguished from the aerosol airflow from the second release location to the collection location. As the different ones of the N DNA taggants need not be combined into single long DNA strands, in-the-field determination of what DNA taggant patterns to use is simplified. A saliva simulant can be mixed from separate containers of DNA taggants and would not require complicated field equipment for constructing custom DNA strands.

Testing might also take into account humidity so that evaporation rates can be accurately simulated. At the release locations, collection locations, and elsewhere, humidity and temperature can be recorded, and test results could be adjusted accordingly. For example, if a test showed that there was a certain reduction in traceability from a release location at a release time to a collection location at a collection time and humidity was very low in the tested building or space, the results might be adjusted or flagged to indicate that the reduction in traceability might be different with higher humidity given that the saliva simulant liquid components would evaporate faster in low humidity. Where the evaporation rate of the saliva simulant is comparable or measurably related to actual saliva evaporation rates, those can be taken into account when determining how much aerosol conveyance there might be in the space.

At a collection location, sampling can be done using, for example, a vacuum sampler.

In some embodiments, the vacuum sample is configured to simulate human inhalation so that detection levels of the pathogen simulant correlate well with the probability of human inhalation at the collection location of an actual pathogen emitted at the release location.

Aerosol mobility might simulate transmission of airborne pathogens via a spraying action that approximates human coughing, sneezing, etc. and an air sampling action that approximates human inhalation. Each spray might create a distribution of tracer particle sizes consistent within human respiratory droplet and aerosol range and an air sampler might have a vacuum flow rate similar to breathing that pulls airborne particles on to a filter specialized for small aerosols. Another sampling method might be the use of surface swabs for customers interested in analyzing fomite transmission risk.

Detection levels might be computed for infectious viral loads for respiratory droplets and aerosols, with DNA concentrated in tracers based on the latest virology for a target pathogen or more generally. Polymerase chain reaction (PCR) technology might be used to detect and quantify the DNA taggants. A computer system might compute a difference between a baseline concentration level of DNA copies in each tracer solution and a detection level of each tracer solution found at each collection location in order to establish a quantifiable reduction, perhaps on a logarithmic scale to allow for graphic display of risk thresholds. These might be in the form of a heatmap diagram.

In some testing, a 4-log reduction (e.g., a 10,000-fold decrease) in DNA copies from the baseline to the collection point might be indicated as a diagnostic indicator for low risk of infection.

Example Test Setup

Figure 2:
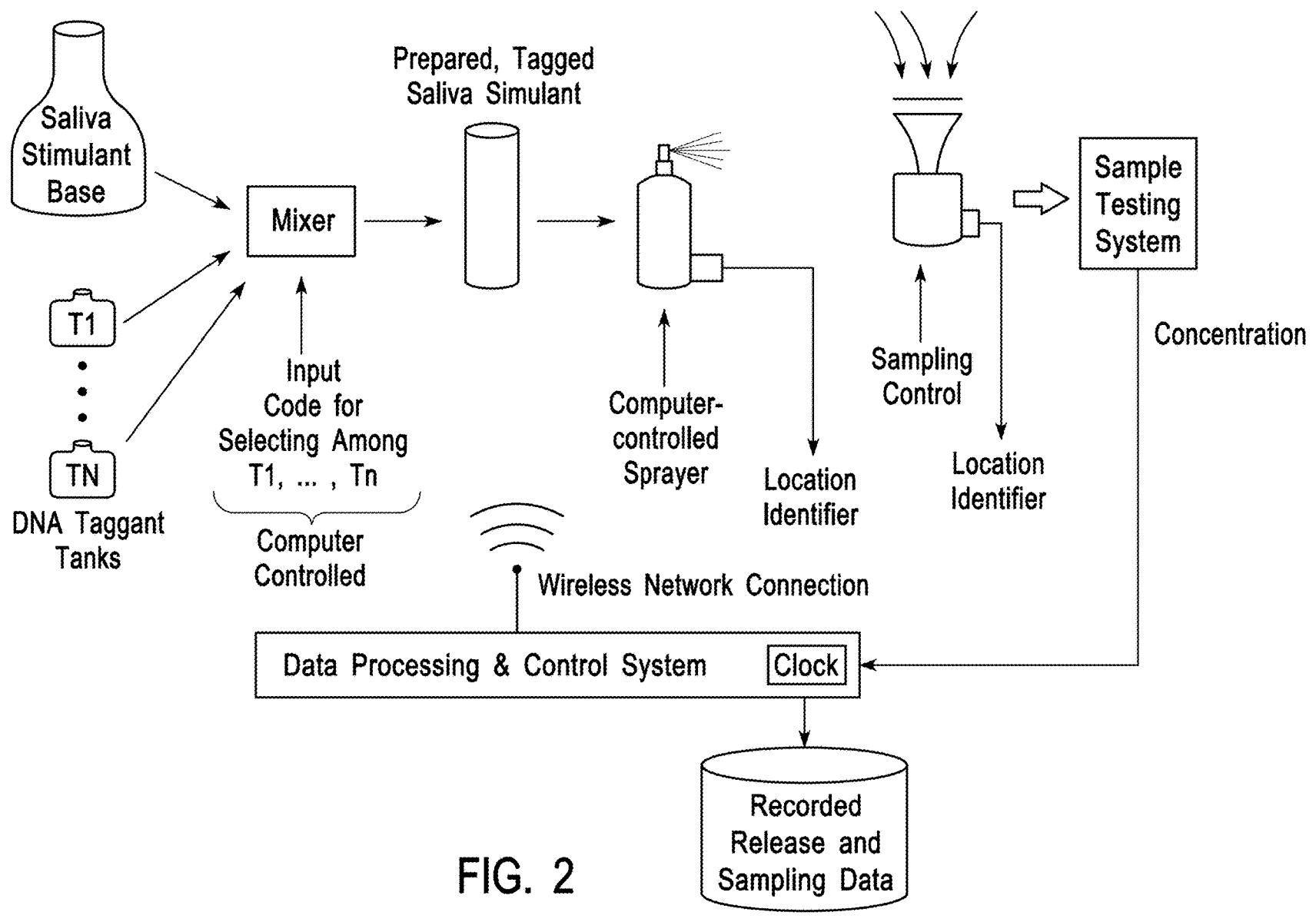

FIG. 2 illustrates an example test setup according to an embodiment. As illustrated there, a mixer might mix saliva simulant with DNA taggants. In other embodiments, one DNA taggant might be used and binding would occur by some process, to result in a prepared and tagged saliva simulant. That can be dispersed by a computer-controlled sprayer that could convey to a data processing and control system the location of the spray, the time, and other details. The data processing and control system might provide instructions to the sprayer as to where to spray and when. The data processing and control system might communicate wirelessly. A sampling controller might control a sampler and also provide data to the data processing and control system. A sample testing system can provide concentration data to the data processing and control system.

Testing and Modeling

FIG. 3 is a simplified depiction of a process 300 for testing and evaluating a space for possible airborne pathogen travel according to an embodiment. As illustrated there, there is (1) a spraying step, (2) a circulation step, (3) a sampling step, and (4) a results step. Prior to the depicted process, an operator might develop a comprehensive test plan of a built space (e.g., an entire building or targeted areas) in coordination with the customer's facilities, EHS, and/or engineering teams. In the spraying step, a test team might release airborne tracers comprising saliva or pathogen simulants, each with its own unique DNA taggant, at selected release locations defined in the test plan. In the circulation step, airborne tracers disperse over specified time period under representative building occupancy conditions to simulate mobility of infectious aerosols, such as travelling through rooms and air ducts. In the sampling step, air samples and/or surface samples are collected and can be tested locally or at certified labs using PCR technology. In the results step, a diagnostic report can be provided with heatmap visualizations, in-depth analysis of high-risk areas, potential remediations, and future testing recommendations. From this, suitable remediation might be taken, as well as critical decisions on space utilization SOPs, HVAC settings, mechanical adjustments, filtration enhancements, and viral inactivation solutions.

Figure 4:
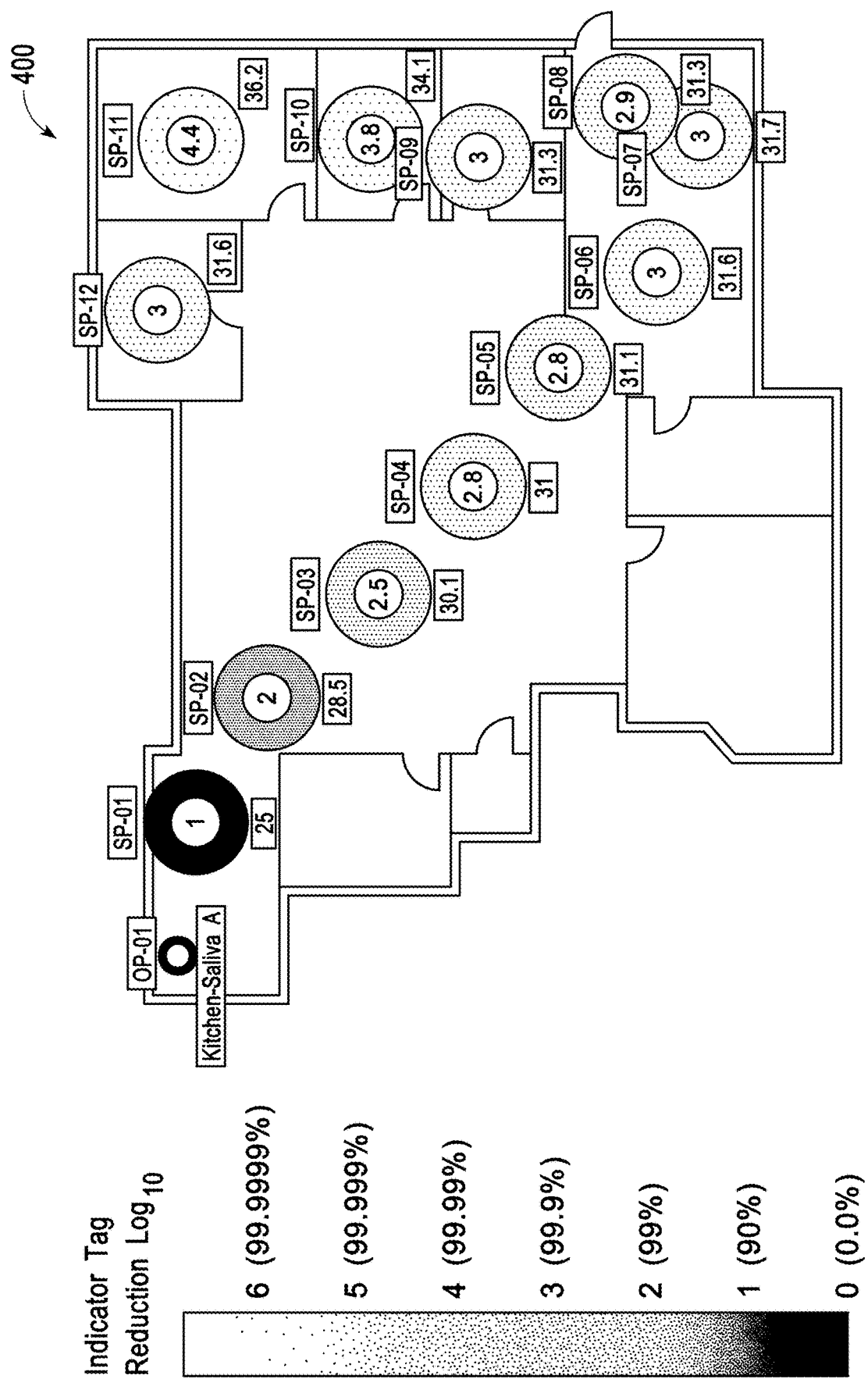
FIG. 4 illustrates a heatmap diagram according to an embodiment.

FIG. 4 is an example heatmap diagram and a heatmap 400 might be used to display test results.

Figure 5:
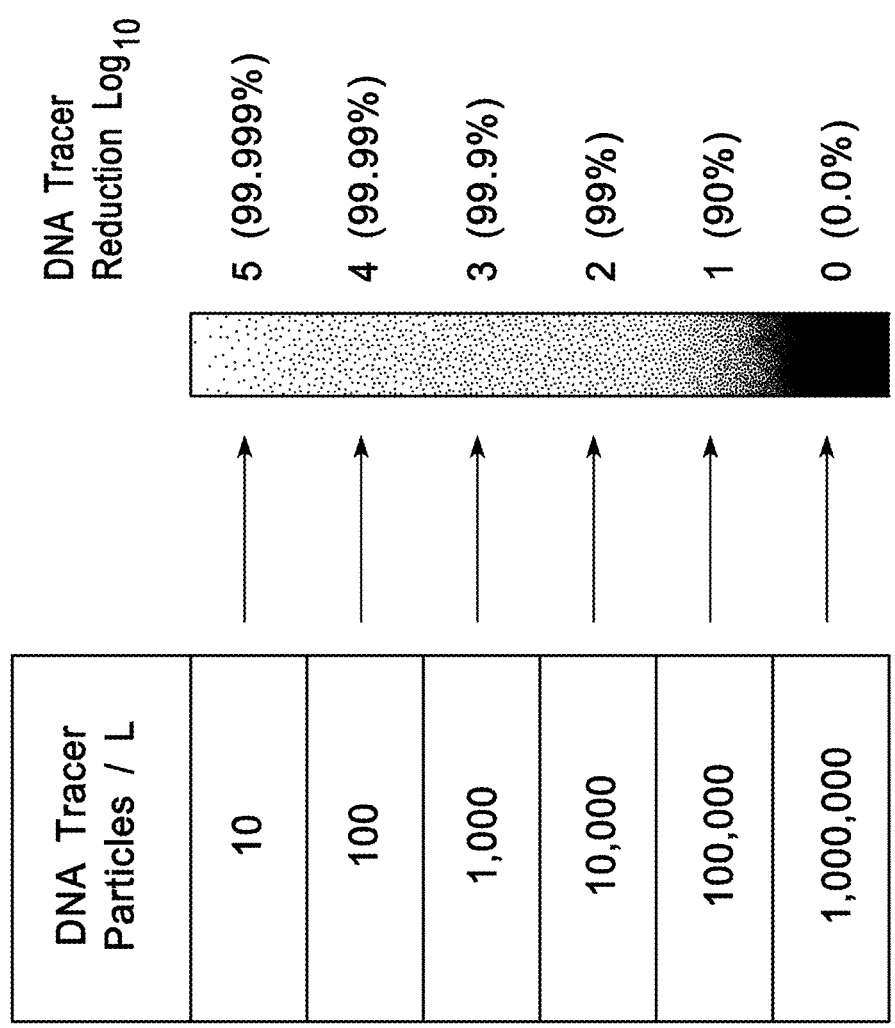
FIG. 5 illustrates a scale that might be used for a heatmap diagram as shown in FIG. 4, according to an embodiment.

FIG. 5 illustrates a scale that might be used for generating heatmap 400, wherein risk thresholds based on logio reduction of DNA copies from a release location to a collection location might be characterized as high risk for a 0- to 1-log reduction, moderate-high risk for a 2-log reduction, moderate-low risk for 3-log reduction, and low risk for 4- or greater log reduction.

Figure 6:
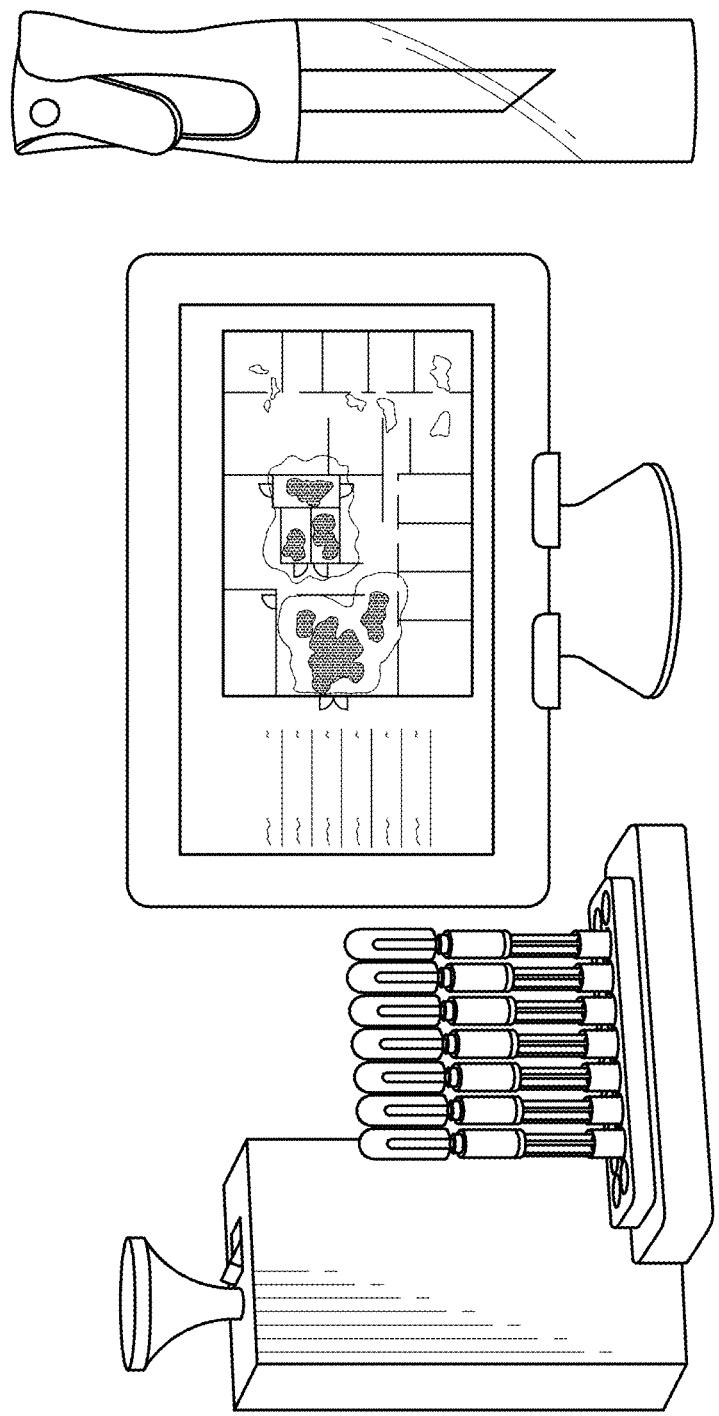
FIG. 6 illustrates an example embodiment of a testing setup.

FIG. 6 illustrates an example embodiment of a testing setup.

FIG. 7 illustrates a building layout 702 and a corresponding bullseye visualization 704 showing detection levels for each tracer tested at a collection location. Written reports might also be generated to show a summary of high-risk areas identified in testing and potential remediations, heatmap visualizations and data tables for each HVAC zone, release location, and collection location. This data could be accumulated over multiple test cycles.

The testing systems described herein are usable for preemptive risk mitigation (e.g., office re-openings) and/or post-viral outbreak response through survey risk assessments and targeted risk assessments.

A survey risk assessment of an indoor space might hotspots, assess ventilation and filtration, verify area isolative efficacy, and inform remediations. In coordination with a test site's facilities management, EHS, and/or engineering teams, a testing systems provider can generate, from computer data and computer models, as well as human input, a test plan based on the particular of the space, such as building size, floor plan, HVAC system configuration, and points of interest and concern, such as restrooms, conference rooms, hallways, elevators, etc.

The testing systems provider can also generate, from test data or otherwise, test scenarios based on specific sets of realistic and representative conditions within the space.

A targeted risk assessment might be used for various tests, such as a room recovery test in a specific room. In such tests, the release location and the collection location might be in the same room or near enough to be considered a release and sampling in the same room or subspace, albeit typically having a collection time separated by an informative time period from the release location.

Figure 8:
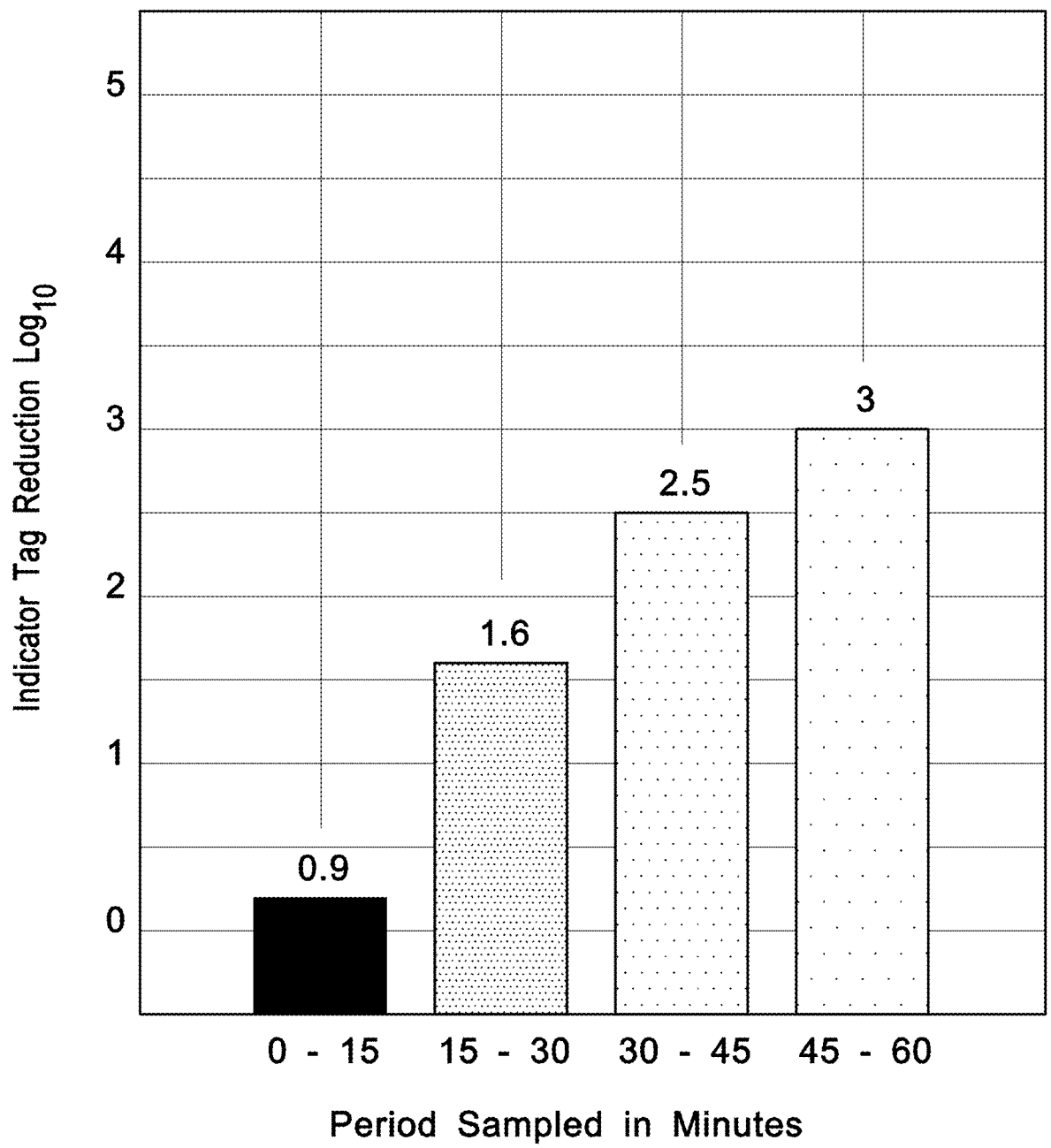
FIG. 8 illustrates an example of results of a room recovery test according to an embodiment.

FIG. 8 illustrates an example of results of a room recovery test. In a room recovery test, several samplings might be done at different collection times, which can determine the time and conditions required to reduce tracer detection to a low risk level (i.e., 3-log reduction or greater) in a specific room or area. This test can be useful for assessing the risk of indoor spaces with high-risk factors, including enclosed areas, poorly ventilated areas, high density occupancy areas, and high-trafficked areas. Examples include restrooms, conference rooms, elevators, lobbies, etc. The resulting data can inform decisions on space utilization, ventilation, filtration, and airborne disinfecting solutions (e.g., UVGI, bipolar ionization).

These tests can measure impacts of HVAC settings on tracer reduction, which would represent reduction in pathogens migrating from a release location in normal operation to a collection location, such as analyzing impact of air changes, airflow, outside air, and positive and negative pressurization for infection control.

These tests can also determine impacts of filtration level on tracer reduction for analyzing the impact of different MERV filter levels, including portable HEPA filters, for infection control. These tests can be done regularly, to provide for on-going risk assessments, either on a time- (e.g., monthly, quarterly, seasonally) or condition-based (e.g., HVAC system seasonal rebalance or linked to a phased reopening plan) schedule in order to capture an indoor space's changing risk profile and/or to collect longitudinal data to track performance over time and support healthy building programs.

Examples of indoor spaces, or other confined spaces which could contain release locations and collection locations might include office buildings, retail locations, food processing plants, manufacturing plants, healthcare and long-term care facilities, education and higher education facilities, hotels and hospitality facilities, correctional facilities, sports and physical fitness facilities, entertainment production studios and sets, and the like.

These tests can be used to objectively measure remediation efforts by testing pre-remediation and post-remediation.

Method Example

Figure 9:
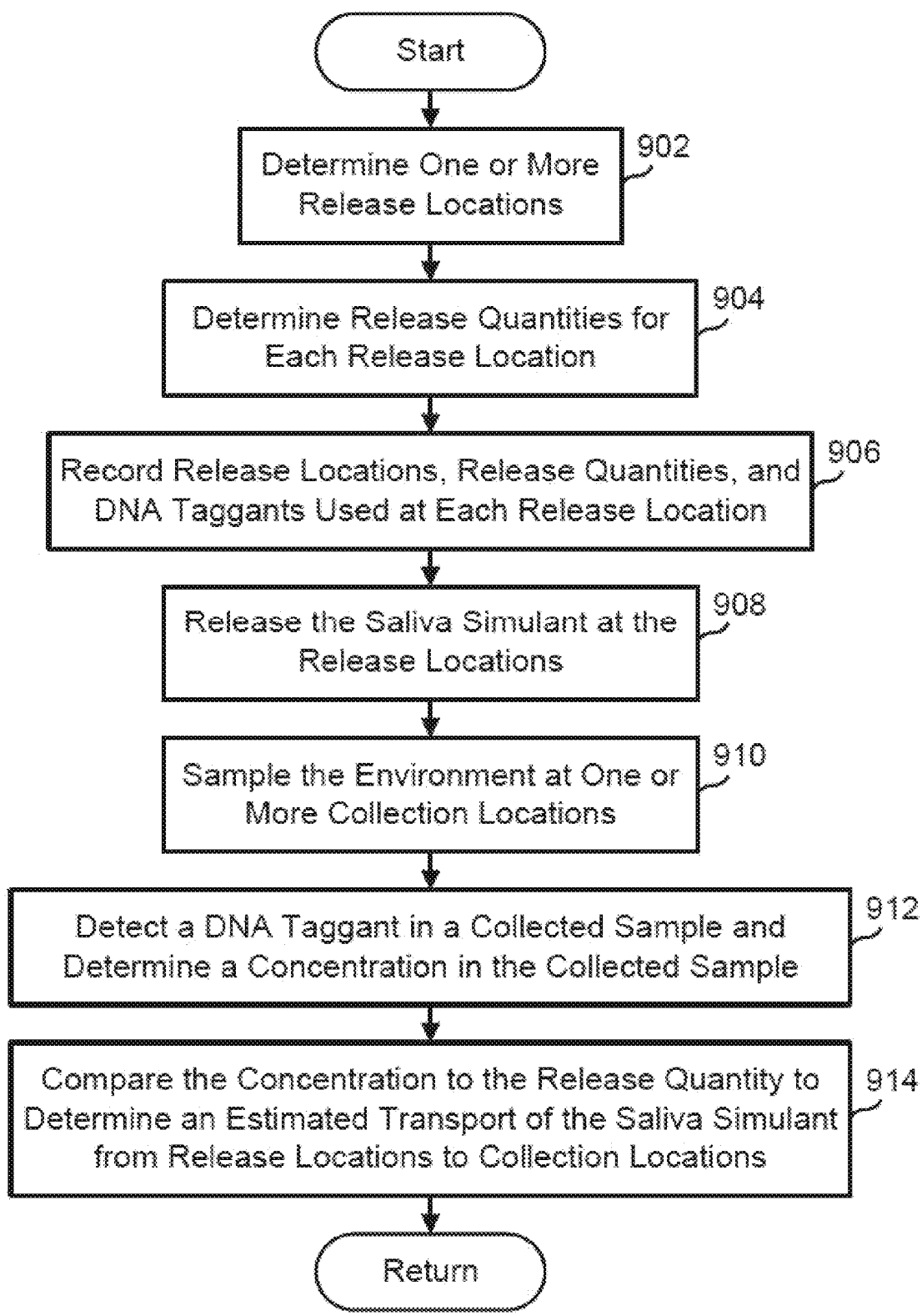
FIG. 9 is a flowchart of a method according to an embodiment.

FIG. 9 is a flowchart of a method according to an embodiment. As illustrated there, the method might have a step 902, in which a computer or person determines one or more release locations. In step 904, quantities for each release location are determined. In step 906, release locations, release quantities, and DNA taggants to be used at each release location are determined. The DNA taggants might be used according to a binary pattern as explained herein. In step 908, the saliva simulant is released at the release locations at release times, each of which might be recorded. In step 910, an environment at one or more collection locations at one or more collection times might be measured, sampled, and recorded. In some embodiments, the sampling occurs at the collection location/time, is sealed or preserved, and is later analyzed at another location and/or another time.

In step 912, a DNA taggant is detected in a collected sample (whether at the collection location or elsewhere) and a concentration in the collected sample is determined. This can be compared to the release details to determine a ratio of release to collection concentrations. In step 914, the concentrations are compared to the release quantity to determine an estimated transport of the saliva simulant from release locations to collection locations.

Hardware Examples

Figure 10:
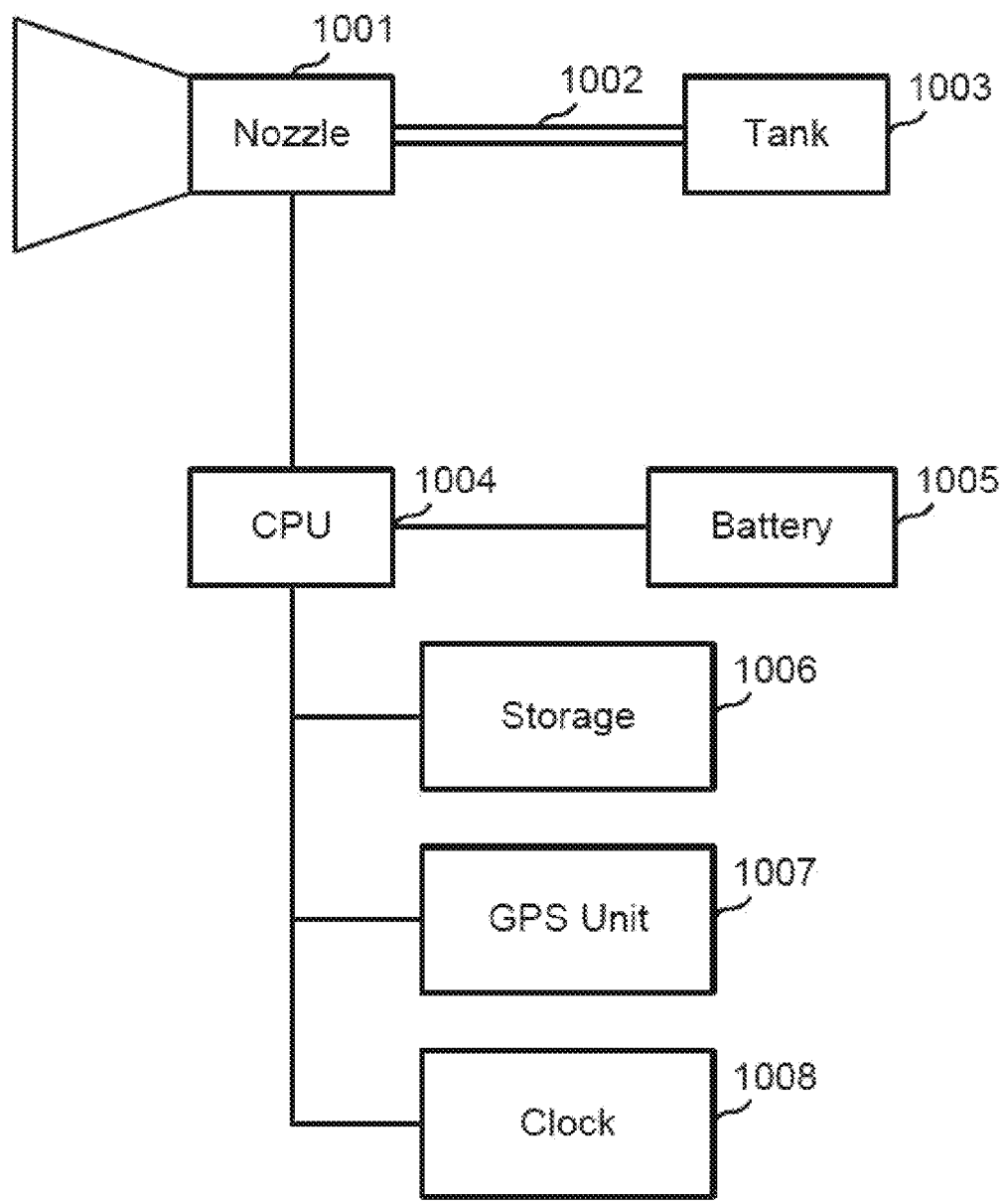
FIG. 10 shows a block diagram of an exemplary application device according to an embodiment.

FIG. 10 shows a block diagram of an exemplary application device, in this case a sprayer having a nozzle 1001 connected to a tank 1003 by a tube (such as a pipe or plastic tubing) 1002. Nozzle 1001 can be electrically connected to a CPU 1004, allowing CPU 1004 to record into a storage element 1006 any actuations of nozzle 1001. CPU 1004 may be connected to a GPS unit 1007, allowing CPU 1004 to also record a location of actuation in storage element 1006, possibly representing a release point. Other methods of automatic location where GPS is not available might be used, such as building sensor detection or manual location entry. CPU 1004 may also be connected to a clock 1008 to allow CPU 1004 to record the date and time of actuation. A battery 1005 may be electrically connected to CPU 1004 to provide power to CPU 1004 and possibly also nozzle 1001.

According to one embodiment, the techniques described herein are implemented by one or generalized computing systems programmed to perform the techniques pursuant to program instructions in firmware, memory, other storage, or a combination. Special-purpose computing devices may be used, such as desktop computer systems, portable computer systems, handheld devices, networking devices or any other device that incorporates hard-wired and/or program logic to implement the techniques.

Figure 11:
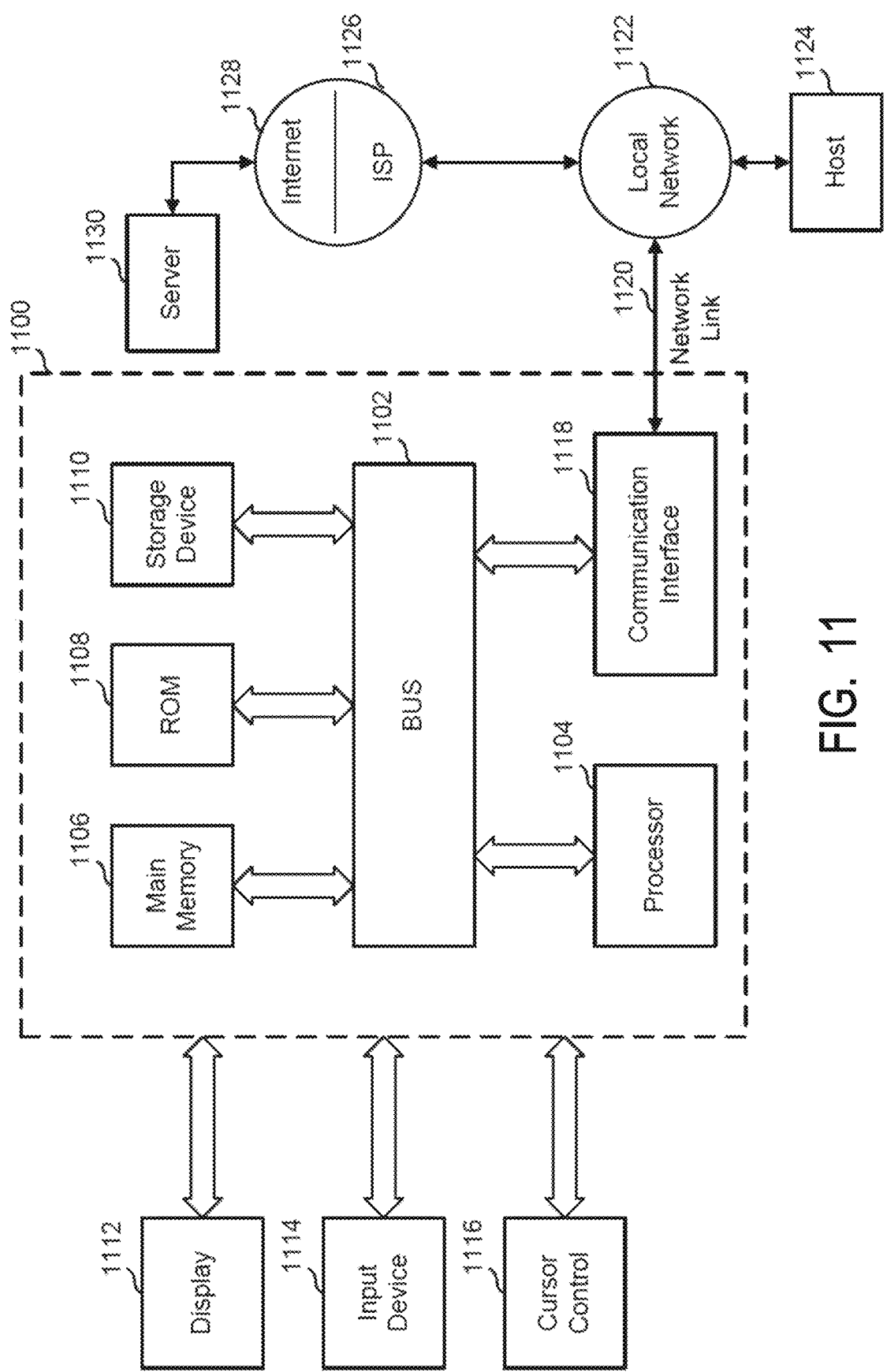
FIG. 11 is a block diagram that illustrates a computer system upon which an embodiment of the invention may be implemented.

For example, FIG. 11 is a block diagram that illustrates a computer system 1100 upon which an embodiment of the invention may be implemented. Computer system 1100 includes a bus 1102 or other communication mechanism for communicating information, and a processor 1104 coupled with bus 1102 for processing information. Processor 1104 may be, for example, a general-purpose microprocessor.

Computer system 1100 also includes a main memory 1106, such as a random-access memory (RAM) or other dynamic storage device, coupled to bus 1102 for storing information and instructions to be executed by processor 1104. Main memory 1106 also may be used for storing temporary variables or other intermediate information during execution of instructions to be executed by processor 1104. Such instructions, when stored in non-transitory storage media accessible to processor 1104, render computer system 1100 into a special-purpose machine that is customized to perform the operations specified in the instructions.

Computer system 1100 further includes a read only memory (ROM) 1108 or other static storage device coupled to bus 1102 for storing static information and instructions for processor 1104. A storage device 1110, such as a magnetic disk or optical disk, is provided and coupled to bus 1102 for storing information and instructions.

Computer system 1100 may be coupled via bus 1102 to a display 1112, such as a computer monitor, for displaying information to a computer user. An input device 1114, including alphanumeric and other keys, is coupled to bus 1102 for communicating information and command selections to processor 1104. Another type of user input device is cursor control 1116, such as a mouse, a trackball, or cursor direction keys for communicating direction information and command selections to processor 1104 and for controlling cursor movement on display 1112. This input device typically has two degrees of freedom in two axes, a first axis (e.g., x) and a second axis (e.g., y), that allows the device to specify positions in a plane.

Computer system 1100 may implement the techniques described herein using customized hard-wired logic, one or more ASICs or FPGAs, firmware and/or program logic which in combination with the computer system causes or programs computer system 1100 to be a special-purpose machine. According to one embodiment, the techniques herein are performed by computer system 1100 in response to processor 1104 executing one or more sequences of one or more instructions contained in main memory 1106. Such instructions may be read into main memory 1106 from another storage medium, such as storage device 1110. Execution of the sequences of instructions contained in main memory 1106 causes processor 1104 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 1110. Volatile media includes dynamic memory, such as main memory 1106. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, an EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 1102. Transmission media can also take the form of acoustic or light waves, such as those generated during radio-wave and infra-red data communications.

Various forms of media may be involved in carrying one or more sequences of one or more instructions to processor 1104 for execution. For example, the instructions may initially be carried on a magnetic disk or solid-state drive of a remote computer. The remote computer can load the instructions into its dynamic memory and send the instructions over a network connection. A modem or network interface local to computer system 1100 can receive the data. Bus 1102 carries the data to main memory 1106, from which processor 1104 retrieves and executes the instructions. The instructions received by main memory 1106 may optionally be stored on storage device 1110 either before or after execution by processor 1104.

Computer system 1100 also includes a communication interface 1118 coupled to bus 1102. Communication interface 1118 provides a two-way data communication coupling to a network link 1120 that is connected to a local network 1122. For example, communication interface 1118 may be a digital network card, cable modem, satellite modem, or a modem to provide a data communication connection to a corresponding type of telephone line. Wireless links may also be implemented. In any such implementation, communication interface 1118 sends and receives electrical, electromagnetic or optical signals that carry digital data streams representing various types of information.

Network link 1120 typically provides data communication through one or more networks to other data devices. For example, network link 1120 may provide a connection through local network 1122 to a host computer 1124 or to data equipment operated by an Internet Service Provider (ISP) 1126. ISP 1126 in turn provides data communication services through the world-wide packet data communication network now commonly referred to as the "Internet" 1128. Local network 1122 and Internet 1128 both use electrical, electromagnetic or optical signals that carry digital data streams. The signals through the various networks and the signals on network link 1120 and through communication interface 1118, which carry the digital data to and from computer system 1100, are example forms of transmission media.

Computer system 1100 can send messages and receive data, including program code, through the network(s), network link 1120 and communication interface 1118. In the Internet example, a server 1130 might transmit a requested code for an application program through Internet 1128, ISP 1126, local network 1122 and communication interface 1118. The received code may be executed by processor 1104 as it is received, and/or stored in storage device 1110, or other non-volatile storage for later execution.

Figure 12:
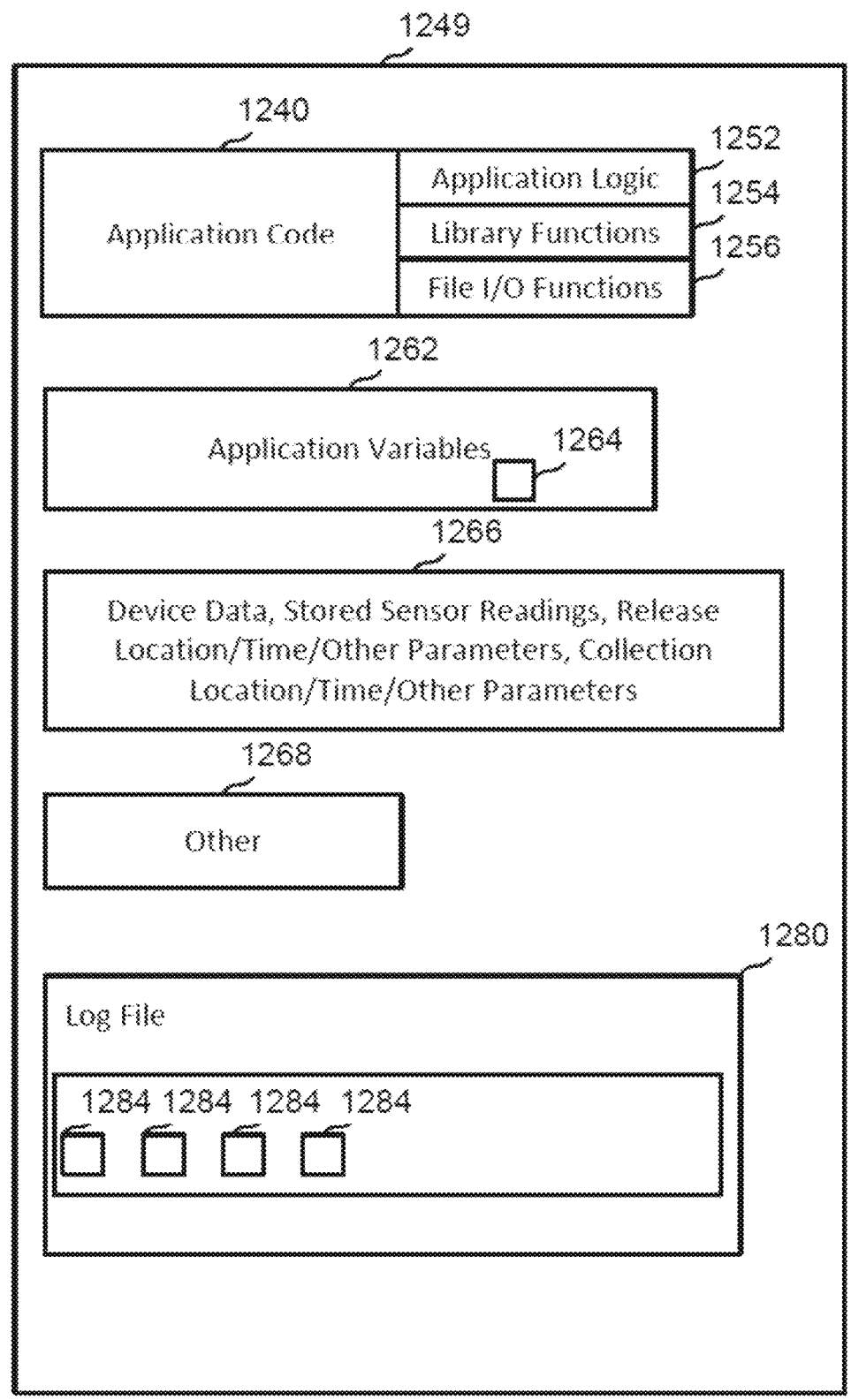
FIG. 12 illustrates structures that might be used by a processor to perform functions described herein and used by the processor to implement elements of the embodiments described herein.

FIG. 12 illustrates structures that might be used by a processor to perform functions described herein and used by the processor to implement elements of the embodiments described herein. For example, where a functional block is referenced, it might be implemented as program code stored in memory. This might be implemented as part of a computer control for a taggant dispenser. The taggant dispenser might be implemented as a stand-alone system, wherein an operator inputs a tag string and the taggant dispenser disperses the appropriate dispersant based on that tag string. The taggant dispenser might be implemented as an integrated system wherein a remote computing platform sends instructions to the taggant dispenser with instructions on which tag string to use, how long to flush, what feedback to provide, etc.

FIG. 12 is a simplified functional block diagram of a storage device 1248 having an application that can be accessed and executed by a processor in a computer system. The application can be one or more of the applications described herein, running on servers, clients or other platforms or devices and might represent memory of one of the clients and/or servers illustrated elsewhere. Storage device 1248 can be one or more memory devices that can be accessed by a processor and storage device 1248 can have stored thereon application code 1250 that can be configured to store one or more processor readable instructions. The application code 1250 can include application logic 1252, library functions 1254, and file I/O functions 1256 associated with the application.

Storage device 1248 can also include application variables 1262 that can include one or more storage locations configured to receive input variables 1264. The application variables 1262 can include variables that are generated by the application or otherwise local to the application. The application variables 1262 can be generated, for example, from data retrieved from an external source, such as a user or an external device or application. The processor can execute the application code 1250 to generate the application variables 1262 provided to storage device 1248.

Application variables 1262 might include operational details needed to perform the functions described herein. Device data 1266 might include details such as tag string lookup tables, stored sensor readings and the like and other details needed. One or more memory locations can be configured to store device data 1266. Device data 1266 can include data that is sourced by an external source, such as a user or an external device.

Storage device 1248 can also include a log file 1280 having one or more storage locations 1284 configured to store results of the application or inputs provided to the application. For example, the log file 1280 can be configured to store a history of actions, alerts, error message and the like.

Airborne Respiratory Droplet and Pathogen Simulants

As described herein, one method uses unique DNA-coded particles, sized and formulated to mimic specific airborne pathogens, such as SARS-CoV-2, to simulate airborne mobility of a respiratory droplet, such as saliva, or of a pathogen of interest, thus providing airborne pathogen simulants. Dispersion of the airborne respiratory droplet and pathogen simulants can be controlled via aerosol liquid or powder placed in or near HVAC and air filtration systems. The airborne respiratory droplet and pathogen simulants can be detected through air samplers at collection locations and processing results through rapid on-site PCR test in order to track particle dispersion. Other tagging and/or dispersion and/or sampling methods might be used.

In one approach, a respiratory droplet simulant or pathogen simulant contains a taggant, such as a distinguishable DNA sequence that is not an active DNA sequence. In a test of a space, multiple distinct respiratory droplet simulants or pathogen simulants might be deployed, as simulants for the same pathogen or distinct pathogens, with each pathogen simulant released at an origin point. Test samples can be taken at different sample sites to test which pathogen simulants traveled to sample sites. By having distinguishable taggants, test results from one sample site can be traced back to multiple origin points. For example, respiratory droplet simulants or pathogen simulants $P_1$, $P_2$, and $P_3$ might be released at origin points $OP_1$, $OP_2$, $OP_3$, respectively. A test at a sample site $S_A$ might pick up instances of each of the respiratory droplet simulants or pathogen simulants, but their presences and concentrations at sample site $S_A$ can be distinguished from each other because they have distinguishable taggants. The taggants might be as described in Zografos I, Zografos II, and/or Zografos III. Taggants that are Generally Recognized As Safe (GRAS) according to the FDA might be used.

Respiratory droplet mobility can be simulated, or viral transmission via airborne liquid droplets and aerosols can be simulated, by dispensing (spraying) a volume of liquid saliva simulant (99% water, 1% protein, and other, for example) tagged with DNA in a concentration, wherein the concentration could be a similar concentration to virus copies (e.g., the number of DNA molecules per ml of saliva simulant might be selected to match a particular number or range of virus copies per ml). A simulation or test might be done by selecting particular mixes and parameters to well-simulate various activities, such as selecting a volume of dispersant and a particle size distribution such that they simulate a cough, a sneeze, talking, breathing during exercise/exertion, or some other human source.

The DNA tagged respiratory droplet simulant might evaporate in a similar fashion to saliva, thus reducing liquid particle size and increasing DNA concentration over time. In the time it takes for dispensed liquid particles to transport through the air and before they hit a surface, many of these particles will reduce from droplet size of greater than 10 µm to aerosol size (e.g., less than 5 µm or some size based on mobility factors) to become much more mobile. In some examples, the dispersion at a release location is particles 0.5 µm to 1 µm in size. The liquid used might have a characteristic that causes it to evaporate at rates similar to saliva evaporation rates in air.

Typical use cases might be to evaluate potential airborne viral mobility in buildings, transportation vehicles and other enclosed or open areas. There is no requirement to have an empty building as the pathogen simulant, such as a saliva simulant is safe to use in occupied spaces.

Having described embodiments in detail, it will be apparent that modifications, variations, and equivalent embodiments are possible without departing from the scope of the invention defined in the appended claims. Furthermore, it should be appreciated that all examples in the present disclosure are provided as non-limiting examples.

EXAMPLES

The following non-limiting examples are provided to further illustrate embodiments disclosed herein. It should be appreciated by those of skill in the art that the techniques disclosed in the examples that follow represent approaches that have been found to function well in practice, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Airborne Pathogen Mobility Testing within a Building

In a building case, an exemplary procedure is as follows:
a) Sampling stations (airborne and surface swab) are mapped out;
b) Origin points/dispense stations are mapped out (these can be mobile, for example to simulate walking down a hallway and dispensing);
c) Each release at a dispense station might use a different DNA taggant, and they can be dispensed sequentially or all together;
d) Samples are collected at a specified time at sampling stations after dispensing is finished (sample collection might be part of a timed process, wherein a period between an origin point and a sample time might be selected to align with a characteristic of a pathogen being simulated, such as selecting a period based on pre-determined durations of viability of the pathogen);
e) Each sample is tested for each dispense station DNA taggant;
f) From the testing result, a determination on effects and transport of the airborne pathogen simulant.

Example 2

Airborne Pathogen Mobility Testing within an Enclosed Area

In an enclosed space, like a conference room, restroom or even a large hotel ballroom, a process might be:
a) set up air samplers in sets typically 6× at each location in one or more locations around the enclosed area;
b) expose the room to specific DNA tagged solutions by spraying DNA tagged solutions. These can be one or more tags at one or more locations in the enclosed area.
c) air samples are collected at a fixed amount of time, such as five, ten, twenty minutes or some other time period using one air sampler;
d) after the predetermined collection period, turn that air sampler off and start another one;
e) repeat for the entire test time cycle (for example, in a sixty-minute test, air samplers might run in ten-minute periods, to gather six samples);
f) tabulate air sample results and optionally use a log reduction dilution as a threshold to declare the enclosed area "safe", typically 4-log reduction (10,000× dilution).

A particular threshold might be more or less than a 4-log reduction, and might be driven by indoor space operator requirements, clinical data for specific pathogens, and/or testing conditions.

A recovery time might be determined as the time where the sampler which has a 4-log reduction or greater result. For example, if a 45-60 min air sampler showed a 4-log reduction from a baseline, that might be usable as an indication that the room might be mostly exhausted and moderately safe after sixty minutes of exposure. This is useful in helping clients understand how to utilize enclosed areas and to confirm HVAC settings and air flows which are needed to achieve reliable dilution to a given log reduction "safe" level.

Example 3

Airborne Pathogen Mobility Testing for Long-Term Exposure

Here, a test might measure long-term exposure, such as a work area that is occupied for a work shift of, say, eight hours. This models the case where an asymptomatic person might be present for an extended period of time while other people are working in the area and might be exposed at differing levels depending on proximity and air flows. The process might be:
a) set up long term emitters of DNA taggant solutions with different tag using humidifiers for four hours, eight hours, or some other periods;
b) set up fixed air samplers around the work area;
c) attach portable air samplers to workers in different areas;
d) set up fixed air samplers outside the work area to get a sense of how far the simulants migrate;
e) then analyze air sample filters to determine the levels of exposure to taggants from emitter locations at each sample location (fixed or mobile).

In some instances, the determination is whether the airborne pathogen simulant as traveled along a given airflow pathway in sufficient measure to indicate the need for mitigation against transport of the pathogen of interest. In some instances, there is an additional sanitation or mitigation step. In some instances, there might be a testing event before the additional sanitation or mitigation step and a testing event after, to measure an effect of the additional sanitation or mitigation step.

Sampling might involve sampling a surface at the sampling station and/or sampling the air at the sampling station. Sampling might be such that a concentration of the pathogen simulant can be determined and compared to a concentration dispersed at the origin points.

FIG. 13 illustrates an example of processing a saliva simulant, which might have been obtained by sampling at a collection point, that contains a DNA taggant bound to a carrier polysaccharide, depicting an electrophoretic mobility shift assay to detect binding of a DNA taggant to a carrier polysaccharide. In particular, FIG. 13 depicts an electrophoretic mobility shift assay for ssDNA:DEAE-Dextran complexes. In that image, column 1 reflects mobility of 1% DEAE-Dextran 40 kDa+70-bases DNA, column 2 reflects mobility of 0.5% DEAE-Dextran 40 kDa+70-bases DNA, column 3 reflects mobility of 0.25% DEAE-Dextran 40 kDa+70-bases DNA, and column 4 reflects mobility of 70-bases DNA.

Figure 14:
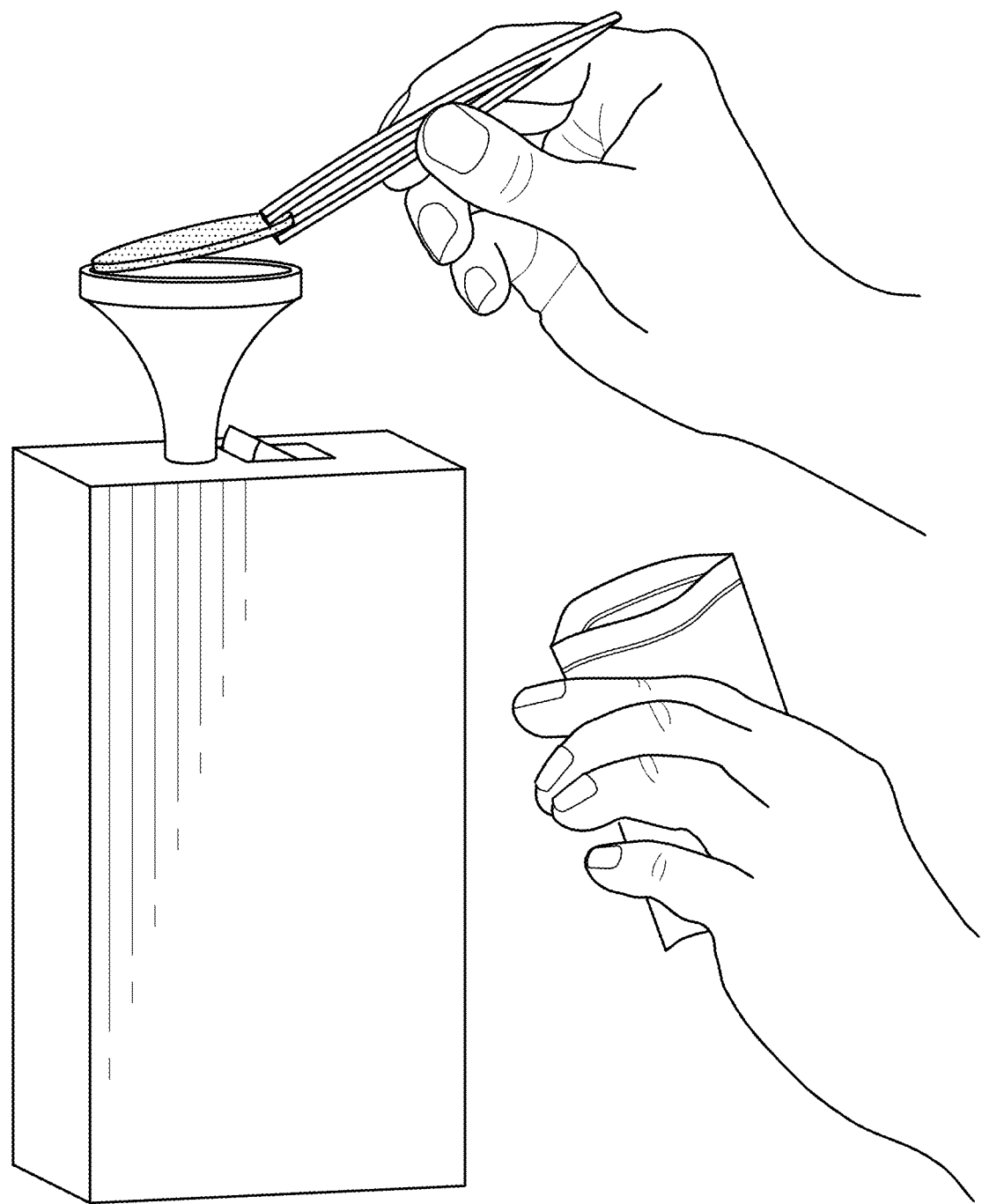
FIG. 14 illustrates an example embodiment of a sampling device.

FIG. 14 illustrates an example embodiment of a sampling device.

Various methods and techniques described above provide a number of ways to carry out the embodiments described. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included, and others specifically excluded, in diverse embodiments.

Although the application has been disclosed in the context of certain embodiments and examples, it will be understood by those skilled in the art that the embodiments of the invention extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context.

The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory. The code may also be provided carried by a transitory computer readable medium e.g., a transmission medium such as in the form of a signal transmitted over a network.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

The use of examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

Further embodiments can be envisioned to one of ordinary skill in the art after reading this disclosure. In other embodiments, combinations or sub-combinations of the above-disclosed invention can be advantageously made. The example arrangements of components are shown for purposes of illustration and combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the invention. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Embodiments of the disclosure can be described in view of the following clauses:
1. A composition comprising a saliva simulant, wherein the saliva simulant comprises a DNA taggant, water, and a carrier, the saliva simulant having been determined or characterized to have a behavior suitable for simulating human emission of a target pathogen.
2. The composition of clause 1, wherein the target pathogen is SARS-Cov-2.
3. The composition of clause 1, wherein the carrier comprises polysaccharides, proteins, salt, or a combination thereof.
4. The composition of clause 3, formed by binding the DNA taggant to a carrier polysaccharide and/or one or more protein to form particles in solution having diameters of 0.01 μm to 100 μm, preferably 0.1 μm to 1 μm.
5. The composition of clause 3, wherein the polysaccharides comprise one or more of maltodextrin, cationic polysaccharides, and DEAE-Dextran.
6. The composition of clause 3, wherein the proteins are single strand DNA binding proteins EcoSSB.
7. The composition of clause 3, further comprising one or more additional carriers to form a saliva simulant solution containing around 99% $H_2O$, and around 1% of a mixture of polysaccharides, proteins, salt and DNA taggants.
8. The composition of clause 1, wherein the behavior of the saliva simulant is suitable for simulating human coughing, sneezing, talking, yelling, and/or singing
9. The composition of clause 1, wherein the behavior of the saliva simulant corresponds to human aerosol emission.
10. The composition of clause 1, wherein the behavior of the saliva simulant corresponds to human droplet emission.
11. The composition of clause 1, wherein the behavior of the saliva simulant corresponds to human droplet emission followed by at least partial evaporation to become aerosolized.
12. A method of providing a saliva simulant, comprising: combining a DNA taggant with water and a carrier to form the saliva simulant, and determining that the saliva simulant has a behavior suitable for simulating human emission of a target pathogen.
13. A method of distributing a saliva simulant, comprising: receiving the saliva simulant, wherein the saliva simulant comprises water, a DNA taggant, and a carrier, and wherein the saliva simulant is characterized in having a behavior suitable for simulating human emission of a target pathogen, and spraying the saliva simulant at a first release location, to be detected at a first collection location.
14. The method of clause 13, wherein the first release location and the first collection location are separated by building infrastructure and wherein the first release location and the first collection location are such that measurable airflow occurs from the first release location to the first collection location.
15. The method of clause 13, wherein the first release location and the first collection location are both within a confined space in a building, the method comprising releasing the saliva simulant at the first release location at a first time and collecting a portion of released saliva simulant at the first collection location at a second time, wherein the second time is after, and distinct from, the first time.
16. The method of clause 13, further comprising: mapping a plurality of collection locations, mapping a plurality of release locations, releasing a selected DNA taggant at a release location, collecting droplet and/or aerosol sample at a collection location of the plurality of collection locations, and quantifying DNA concentrations at collection locations using qPCR.
17. The method of clause 16, wherein at least some of the plurality of release locations are mobile and simulate dispersing while moving.
18. The method of clause 16, wherein releasing comprises releasing a plurality of releases using a plurality of DNA taggants or combinations thereof.
19. A method of detecting a pathogen simulant, comprising: determining a plurality of locations to receive a saliva simulant released in air, wherein the saliva simulant comprises water, a DNA taggant, and a carrier, the saliva simulant having been determined or characterized to have a behavior suitable for simulating human emission of a target pathogen, collecting a sample at each location of the plurality of locations, and determining an amount of the saliva simulant in the sample.

20. A sprayer for spraying a saliva simulant, comprising: a container containing the saliva simulant, wherein the saliva simulant comprises water, a DNA taggant, and a carrier, a trigger connected to the container and configured to spray the saliva simulant out into an airspace at a rate that corresponds to saliva dispersion of a human into the airspace resulting from the human coughing, sneezing, talking, yelling, and/or singing.

21. An air sampler for collecting an air sample, comprising: a vacuum apparatus configured to collect the air sample from an ambient environment and to have a vacuum flow rate that matches human breathing, and a filter connected to the vacuum apparatus and configured to have a pore size suitable for filtering a saliva simulant from the air sample.

22. A system comprising: a sprayer configured to release a saliva simulant, and an air sampler configured to collect an air sample at a plurality of locations determined to receive a portion of released saliva simulant released in air.

23. A method for displaying movement of a saliva simulant, comprising: receiving information of a first amount of the saliva simulant at a first location where the saliva simulant is released in air and of a second amount of the saliva simulant detected a second location that is different from the first location, wherein the saliva simulant comprises water, a DNA taggant, and a carrier, the saliva simulant having been determined or characterized to have a behavior suitable for simulating human emission of a target pathogen, and generating a report displaying a first graphic element representing the first amount of the saliva simulant at the first location and displaying a second graphic element representing the second amount of the saliva simulant at the second location in a map comprising the first location and the second location.

What is claimed is:

1. A method of distributing a saliva simulant, comprising:
   receiving the saliva simulant, wherein the saliva simulant comprises water, a DNA taggant, and a carrier, and wherein the saliva simulant simulates human emission of a target pathogen;
   spraying the saliva simulant in air at a first release location in a determined release amount, to be detected at a first collection location, wherein a detected amount of the saliva simulant detected at the first collection location relative to the determined release amount is indicative of a degree of airflow from the first release location to the first collection location;
   collecting a sample at the first collection location;
   determining a tracer concentration at the first collection location based on the detected amount of the saliva simulant detected at the first collection location;
   determining a scale that correlates tracer concentrations to inhalation probabilities and/or viral load;
   based on the collected amount and/or the tracer concentration, and based on the scale, determining an infection risk value representing infection risk in an enclosed space diagnostic of infection by the target pathogen; and
   generating a report displaying a first graphic element representing the infection risk value and displaying a second graphic element representing the detected amount of the saliva simulant at the first collection location in a map comprising the first release location and the first collection location.

2. The method of claim 1, wherein the first release location and the first collection location are distinct locations in a building and are separated, at least in part, by a portion of a building layout that blocks airflow and wherein the first release location and the first collection location are such that measurable airflow occurs from the first release location to the first collection location, flowing around the portion of the building layout that blocks the airflow.

3. The method of claim 1, wherein the first release location and the first collection location are both within a confined space in a building, the method comprising releasing the saliva simulant at the first release location at a first time and collecting a portion of released saliva simulant at the first collection location at a second time, wherein the second time is after, and distinct from, the first time.

4. The method of claim 1, further comprising:
   mapping a plurality of collection locations;
   mapping a plurality of release locations;
   releasing a selected DNA taggant at a release location;
   collecting droplet and/or aerosol sample at a collection location of the plurality of collection locations; and
   quantifying DNA concentrations at collection locations using qPCR.

5. The method of claim 4, wherein at least some of the plurality of release locations are mobile and simulate dispersing while moving.

6. The method of claim 4, wherein releasing comprises releasing a plurality of releases using a plurality of DNA taggants or combinations thereof.

7. The method of claim 1, wherein spraying the saliva simulant at the first release location comprises spraying the saliva simulant out into an airspace at a rate that corresponds to saliva dispersion of a human into the airspace resulting from the human coughing, sneezing, talking, yelling, and/or singing.

8. The method of claim 1, wherein the target pathogen is SARS-Cov-2, the carrier is bound to the DNA taggant via a carrier polysaccharide and/or one or more protein to form particles in solution having diameters of 0.01 µm to 100 µm, and one or more additional carriers to form a saliva simulant solution containing around 99% $H_2O$, and around 1% of a mixture of polysaccharides, proteins, salt and DNA taggants.

9. The method of claim 8, wherein the particles in solution have diameters of 0.1 µm to 1 µm.

10. The method of claim 1, further comprising collecting an air sample from an ambient environment at the first collection location with a vacuum apparatus having a vacuum flow rate that matches human breathing, collecting through a filter connected to the vacuum apparatus, the filter having a pore size suitable for filtering the saliva simulant from the air sample.

11. A method of detecting a pathogen simulant, comprising:
    determining a plurality of collection locations to receive at least a portion of the pathogen simulant released in air, wherein the pathogen simulant comprises water, a DNA taggant, and a carrier, the pathogen simulant simulating human emission of a target pathogen, the plurality of collection locations including a first collection location;
    determining a release amount, at least approximately, of the pathogen simulant released in air at a first release location;
    collecting a sample at the first collection location of the plurality of collection locations;
    determining a collected amount of the pathogen simulant in the sample;

determining a tracer concentration at the first collection location based on the collected amount;

determining a scale that correlates tracer concentrations to inhalation probabilities and/or viral load; and based on the collected amount and/or the tracer concentration, and based on the scale, determining an infection risk value representing infection risk in an enclosed space diagnostic of infection by the target pathogen.

12. The method of claim 11, further comprising:

releasing a first amount of the pathogen simulant in air at a first location of the plurality of collection locations;

recording an indication of the first amount;

measuring a second amount of the pathogen simulant in the sample collected at a second location that is different from the first location; and generating a report displaying a first graphic element representing the first amount of the pathogen simulant at the first location and displaying a second graphic element representing the second amount of the pathogen simulant at the second location in a map comprising the first location and the second location.

13. The method of claim 11, wherein the target pathogen is SARS-Cov-2.

14. The method of claim 11, wherein the carrier comprises polysaccharides, proteins, salt, or a combination thereof.

15. The method of claim 14, wherein the pathogen simulant comprises the DNA taggant bound to a carrier polysaccharide and/or one or more protein to form particles in solution having diameters of 0.01 μm to 100 μm.

16. The method of claim 15, wherein the pathogen simulant comprises one or more additional carriers to form a pathogen simulant solution containing around 99% $H_2O$, and around 1% of a mixture of polysaccharides, proteins, salt and DNA taggants.

17. The method of claim 15, wherein the particles in solution have diameters of 0.1 μm to 1 μm.

18. The method of claim 11, wherein the pathogen simulant is a simulant with a behavior corresponding to human aerosol emission and/or human droplet emission.

19. The method of claim 11, wherein the pathogen simulant is a simulant with a behavior corresponding to human droplet emission followed by at least partial evaporation to become aerosolized.

20. The method of claim 11, wherein collecting the sample comprises collecting an air sample from an ambient environment with a vacuum apparatus with a vacuum flow rate that matches human breathing through a filter connected to the vacuum apparatus, the filter having a pore size suitable for filtering the pathogen simulant from the air sample.

21. A method of measuring reduction of potential pathogens in an enclosed space, comprising:

determining a plurality of collection locations in the enclosed space to receive at least a portion of a pathogen simulant released in air, wherein the pathogen simulant comprises water, a DNA taggant, and a carrier, the pathogen simulant simulating human emission of a target pathogen, the plurality of collection locations including a first collection location;

determining a release amount, at least approximately, of the pathogen simulant released in air at a first release location in or around the enclosed space;

collecting a sample at the first collection location of the plurality of collection locations;

determining a collected amount of the pathogen simulant in the sample;

determining a tracer concentration at the first collection location based on the collected amount;

determining a scale that correlates tracer concentrations to inhalation probabilities and/or viral load;

based on the collected amount and/or the tracer concentration, and based on the scale, determining an infection risk value representing infection risk in the enclosed space diagnostic of infection by the target pathogen;

based on the infection risk value, as measured over a plurality of times, determining a recovery time for the enclosed space.

22. The method of claim 21, wherein the recovery time corresponds to a time over which the tracer concentration reduces by a predetermined reduction ratio.

23. The method of claim 22, wherein the predetermined reduction ratio is a ratio of $10^{-4}$ or less, representing a reduction in the tracer concentration over the recovery time by a factor of at least $10^4$.

* * * * *

UNITED STATES PATENT AND TRADEMARK OFFICE
CERTIFICATE OF CORRECTION

PATENT NO. : 12,258,638 B2
APPLICATION NO. : 17/165935
DATED : March 25, 2025
INVENTOR(S) : Ulrike W. Hodges et al.

Page 1 of 1

It is certified that error appears in the above-identified patent and that said Letters Patent is hereby corrected as shown below:

In the Specification

Column 1, Lines 18-21, change:
"(2) U.S. Pat. No. 10,556,032 issued Feb. 11, 2020 to Zografos, et al. entitled "Sanitation Monitoring System Using Pathogen Simulants and Simulant Tracking (hereinafter "Zografos II");"

To:
--(2) U.S. Pat. No. 10,556,032 issued Feb. 11, 2020 to Zografos, et al. entitled "Sanitation Monitoring System Using Pathogen Surrogates and Surrogate Tracking" (hereinafter "Zografos II");--

Column 1, Lines 22-27, change:
"(3) U.S. Pre-Grant Publication 2017/0038353 published Feb. 9, 2017 naming Zografos, et al. and entitled "Pathogen Simulants Based on Encapsulated Tagged DNA for Verification of Sanitation and Wash Water Systems for Fresh Produce" (hereinafter "Zografos III")."

To:
--(3) U.S. Pre-Grant Publication 2017/0038353 published Feb. 9, 2017 naming Zografos, et al. and entitled "Pathogen Surrogates Based on Encapsulated Tagged DNA for Verification of Sanitation and Wash Water Systems for Fresh Produce" (hereinafter "Zografos III").--

Signed and Sealed this
Second Day of September, 2025

Coke Morgan Stewart
*Acting Director of the United States Patent and Trademark Office*